United States Patent [19]
Slanetz et al.

[11] Patent Number: 6,080,840
[45] Date of Patent: *Jun. 27, 2000

[54] SOLUBLE T CELL RECEPTORS

[76] Inventors: Alfred E. Slanetz, 170 Foxbridge Village Rd., Branford, Conn. 06405; Alfred L. M. Bothwell, 188 Janeway Dr., Guilford, Conn. 06437

[ * ] Notice: This patent issued on a continued prosecution application filed under 37 CFR 1.53(d), and is subject to the twenty year patent term provisions of 35 U.S.C. 154(a)(2).

[21] Appl. No.: 08/393,157

[22] Filed: Feb. 17, 1995

Related U.S. Application Data

[63] Continuation-in-part of application No. 08/168,782, Dec. 14, 1993, abandoned, which is a continuation of application No. 07/822,538, Jan. 17, 1992, abandoned.

[51] Int. Cl.[7] .................................................. C07K 14/00
[52] U.S. Cl. ...................... 530/350; 435/69.1; 435/69.8; 435/70.1; 435/252.3
[58] Field of Search ................................ 530/350, 387.1; 435/6, 7.24, 68.1, 69.1, 69.5, 69.8, 70.1, 172.3, 252.3

[56] References Cited

FOREIGN PATENT DOCUMENTS

| 59110438 | 1/1991 | WIPO . |
| 39118019 | 5/1991 | WIPO . |
| 29201715 | 7/1991 | WIPO . |

OTHER PUBLICATIONS

Novotny et al., 1991, Proc. Natl. Acad. Sci. USA 88:8646–8650.
Grégoire et al., 1991, Proc. Natl. Acad. Sci USA 88:8077–8081.
Slanetz et al., "Heterodimeric, disulfide–linked αβ T–cell receptors in solution", *European Journal of Immunology*, 21, 179–183, (Jan., 1991). [Published on or after Jan. 17, 1991].
Gascoigne et al., "Direct binding of secreted T–cell receptor β chain to superantigen associated with class II major histocompatibility complex protein", *Proc. Natl. Acad. Sci. USA*, 88, 613–616 (Jan. 1991).
Lin et al., "Expression of T Cell Antigen Receptor Heterodimers in a Lipid–Linked Form", *Science*, 249, 677–679 (Aug. 1990).
Gascoigne, "Transport and Secretion of Truncated T Cell Receptor β–Chain Occurs in the Absence of Association with CD3", *J. Biol. Chem.*, 265(16), 9296–9301 (Jun. 1990).
Goverman et al., "Chimeric Immunoglobulin–T Cell Receptor Proteins Form Functional Receptors: Implications for T Cell Receptor Complex Formation and Activation", *Cell*, 60, 929–939 (Mar. 1990).
Becker et al., "Expression of a Hybrid Immunoglobulin–T Cell Receptor Protein in Transgenic Mice", *Cell*, 58, 911–921 (Sep. 1989).
Davis et al., "TCR Recognition and Selection In Vivo", *Cold Spring Harbor Symposia on Quantitative Biology, LIV*, 119–128 (Jun. 1989).
Guy et al., "Antigen–Specific Helper Function of Cell–Free T Cell Products Bearing TCR $V_\beta 8$ Determinants", *Science*, 244, 1477–1480 (Jun. 1989).
Mariuzza et al., "Secretion of a Homodimeric $V_\alpha C_\kappa$ T–cell Receptor–Immunoglobulin Chimeric Protein", *J. Biol. Chem.*, 264(13), 7310–7316 (May 1989).
Traunecker et al., "Solubilizing the T–cell receptor–problems in solution", *Immunology Today*, 10(1), 29–32 (1989).
Rebai et al., "Engineered Secreted T–Cell Receptor αβ Heterodimers", *W–12 Structure/function relationships of the T cell receptor complex*, (Abstract 12–11), 55 (1989).
Gascoigne et al., "Secretion of a chimeric T–cell receptor–immunoglobulin protein", *Proc. Nat'l. Acad. Sci. USA*, 84, 2936–2940 (May 1987).
Traunecker et al., "A novel approach for preparing anti–T cell receptor constant region antibodies", *Eur. J. Immunol.*, 16, 851–854 (1986).

*Primary Examiner*—Laurie Scheiner
*Attorney, Agent, or Firm*—Lisa B. Kole

[57] ABSTRACT

An intact, assembled T cell receptor (TcR) in soluble form is provided. The soluble TcR is prepared by splicing the extracellular domains of a T cell receptor to the glycosyl phosphatidylinositol (GPI) membrane anchor sequences of Thy-1. The molecule is expressed in the absence of CD3 on the cell surface, and can be cleaved from the membrane by treatment with phosphatidylinositol specific phospholipase C (PI-PLC). The α and β chains of the soluble molecule are paired in the native conformation as judged by reactivity with the anti-$V_\beta 8$ monoclonal antibody F23.1, and with the anti-clonotypic monoclonal antibody 1B2. The soluble TcR is a disulfide linked dimer with a molecular mass of 95 kDa on SDS-PAGE under nonreducing conditions, and 47 kDa after reduction.

7 Claims, 19 Drawing Sheets

α TCR/Thy-1

HincII / HinPI

TGT GAT GCC ACG TT/C GCG AAT CCC

β TCR/Thy-1

XmnI / AvaI

TGT GGA ATC/TCG GGC GCG AAT CCC

FIG.1B

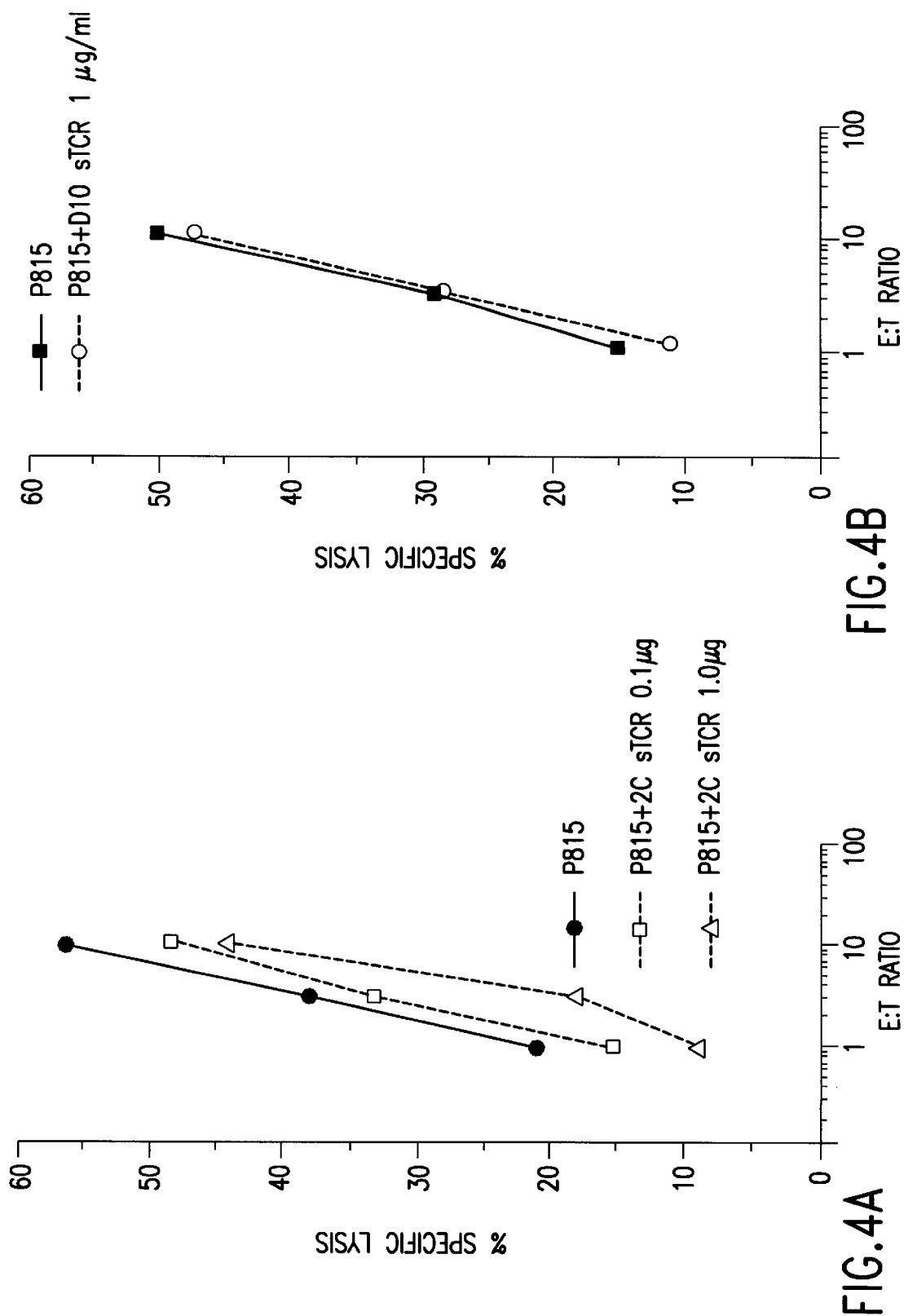

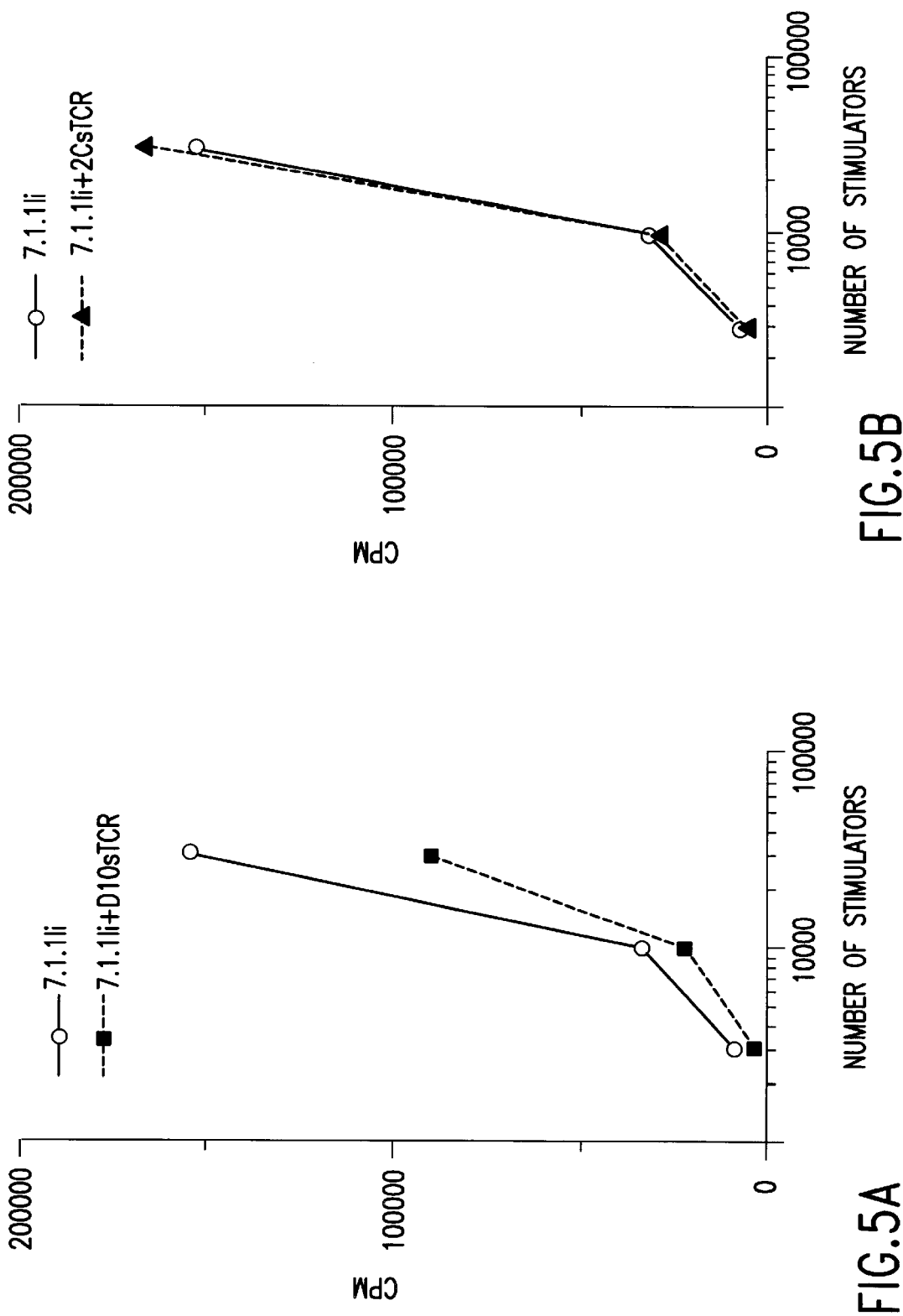

SEQUENCE LISTING (1) GENERAL INFORMATION:

(iii) NUMBER OF SEQUENCES:  2

(2) INFORMATION FOR SEQ ID NO:1:

(i) SEQUENCE CHARACTERISTICS:
        (A) LENGTH:  24 Nucleotides
        (B) TYPE:  Nucleic Acid
        (C) STRANDEDNESS:  Single
        (D) TOPOLOGY:  Linear (ii) MOLECULE TYPE:  DNA (iii) HYPOTHETICAL:

(iv) ANTI-SENSE:  No (vii) IMMEDIATE SOURCE:

(xi) SEQUENCE DESCRIPTION:  SEQ ID NO:1:

TGTGATGCCA CGTTCGCGAA TCCC    24

(2) INFORMATION FOR SEQ ID NO:2:

(i) SEQUENCE CHARACTERISTICS:
        (A) LENGTH: 24 Nucleotides
        (B) TYPE: Nucleic Acid
        (C) STRANDEDNESS: Single
        (D) TOPOLOGY: Linear (ii) MOLECULE TYPE: DNA (iii) HYPOTHETICAL:

(iv) ANTI-SENSE: No (vi) IMMEDIATE SOURCE:

(xi) SEQUENCE DESCRIPTION: SEQ ID NO:2:

TGTGGAATCT CGGGCGCGAA TCCC        24

SOLUBLE T CELL RECEPTORS

This is a continuation-in-part of application(s) U.S. Ser. No. 08/168,782 filed on Dec. 14, 1993, now abandoned, which is a continuation of U.S. Ser. No. 07/822,538 filed Jan. 17, 1992 now abandoned.

BACKGROUND OF THE INVENTION

1. Field of the Invention

The present invention relates to the preparation of heterodimeric, disulfide-linked $\alpha/\beta$ T cell receptors (TcR) in solution.

2. Background of the Related Art

The availability of soluble T cell receptors would allow the isolation and identification of natural and artificial ligands for therapeutic application, and the study of membrane-bound proteins. Proteins and antibodies to soluble T-cell receptors may be used in diagnosis and treatment of autoimmune diseases. For example, in a model immune system, experimental allergic encephalomyelitis, antibodies directed against TcRs inhibited and even reversed the development of the disease. In addition, soluble TcRs may be applicable to preventing rejection during organ transplantation and as therapy to prevent autoimmune diseases.

Structural and functional analysis of T cell receptor-ligand binding would also be greatly advanced by the availability of an intact, assembled TcR in soluble form. The "wild type" TcR processing pathway requires that the TcR $\alpha$ and $\beta$ chains associate with the CD3 components in the endoplasmic reticulum before they are transported to the T cell surface as reported by Clevers et al., *Annu. Rev. Immunol.*, 6, 629 (1988); Alarcon et al., *J. Biol. Chem.*, 263, 2953 (1988); Berkhout et al., *J. Biol. Chem.*, 263, 8528 (1988); Koning et al., *J. Immunol.*, 140, 3126 (1988); and Lippincott-Schwartz et al., *Cell*, 54, 209 (1988). Charged residues within the otherwise hydrophobic transmembrane region may be responsible for these associations, see Morley et al., *J. Exp. Med.*, 168, 1971 (1988). Since the amino terminal variable and junctional regions completely encode T cell receptor antigen specificity and Major Histocompatibility Complex (MHC) restriction, which is the property of a T cell to respond to fragments of antigen complexed to self MHC molecules of other cells, a number of strategies which replace or delete the TcR transmembrane region have been attempted for the production of soluble TcR molecules.

Soluble TcR molecules made using chinese hamster ovary (CHO) cells are described by Lin et al., "Expression of T Cell Antigen Receptor Heterodimers in a Lipid-Linked Form", *Science*, 249, 677–679 (August 1990) and Davis et al., "TCR Recognition and Selection In Vivo", *Cold Spring Harbor Symposia on Quantitative Biology*, LIV, 119–128 (June 1989). Both of these articles describe the use of a GPI linkage approach to produce soluble TcR molecules. However, the soluble TcR molecules utilizing CHO transfectants, rather than using T-cell lymphomas of the present invention, produce soluble TcRs which are structurally and functionally different than those produced by the present invention. The following differences were observed:

1. When testing the CHO cells utilized by Lin et al. and Davis et al., the inventors herein observed that CHO cells fail to produce the clonotypic epitopes, which would indicate that a T-cell specific processing event is necessary for correct T-cell receptor pairing.

2. The molecular weight of the soluble T-cell receptors produced in accordance with Lin et al. and Davis et al. is significantly lower than the molecular weight of bound T-cell receptors and of the soluble T-cell receptor molecules of the present invention.

3. The soluble T-cell receptors reported by Lin et al. and Davis et al. fail to block the T-cell clone of origin. It may be that their molecule is incorrectly processed in CHO transfectants.

4. Due to the lack of of a clonotypic antibody to the 2B4 TcR, the 2B4 $\alpha$ and $\beta$ chains were shown to be associated by crossblocking experiments using anti-$V_\alpha$ and anti-$V_\beta$ specific monoclonal antibodies by FCM analysis. Thus it is impossible to judge if they are correctly paired.

Attempts to produce a soluble counterpart of the membrane bound T cell receptor by fusing TcR variable regions to immunoglobulin constant regions have produced, with one exception, unpaired $\alpha$ and $\beta$ chains, see Traunecker et al., *Immunol. Today*, 10, 29 (1989), and Gascoigne et al., *Proc. Natl. Acad. Sci. USA*, 84, 2936 (1987). These investigators claim to have produced soluble TcRs by techniques other than using the GPI linkage approach of the present invention. For example, Traunecker et al., *Immunol. Today*, 10, 29 (1989), Gascoigne et al., *Proc. Natl. Acad. Sci. USA*, 84, 2936 (1987) and Gascoigne, *J. Biol. Chem.*, 265(16), 9296–9301 (June 1990) describe the use of myeloma cells J558L to produce and secrete a form of the TCR $\beta$ chain. Also see Gascoigne et al., *Proc. Natl. Acad. Sci. USA*, 88, 613–616 (January 1991) which describes the binding of SEA (staphyloccal entertoxin A) Raji cells, a Burkitt lymphoma cell that expresses MHC Class I and II, to piates coated with the soluble $V_\beta$.

Additionally, Mariuzza et al., *J. Biol. Chem.*, 264(13), 7310–7316 (May 1989) utilize J558L myeloma cells to produce soluble $\alpha$ chains of the TcR. Traunecker et al., *Eur. J. Immunol.*, 16, 851–854 (1986); and Becker et al., *Cell*, 58, 911–921 (September 1989) both use these same myeloma cells, however, neither report producing soluble TcR's.

Attempts to produce soluble $\alpha/\beta$ TcR molecules by the introduction of translational termination codons upstream of the TcR transmembrane region have also failed, as reported by Traunecker et al., *Immunol. Today*, 10, 29 (1989), and Gascoigne, *J. Biol. Chem.*, 265, 9296 (1990). These methods include the production of TcRs/immunoglobulin chimeric proteins and the insertion of stop codons in front of the transmembrane portion of the TcR $\alpha$ and $\beta$ chains. These techniques utilized a stop codon to produce unpaired $\alpha$ or $\beta$ chains. Therefore, they produced a molecule which may not be functional, or is structurally quite different than that produced by the present invention. See Rebai et al., *W-12 Structure/function relationships of the T cell receptor complex*, (Abstract 12-11), 55 (1989) which reports production of soluble TcR $\alpha$ and $\beta$ chains using transfected myeloma cell lines. Their work, however, has never been published, and although their molecule is functional, their technique has failed to be broadly applicable to other TcR molecules; see Traunecker et al., (1989) supra. See also Grégoire et al., *Proc. Natl. Acad. Sci., U.S.A.*, 88, 8077–8081, (September 1991) which reports that $V_\alpha C_\alpha C_k$ and $V_\beta C_\beta C_k$ were secreted as non covalent heterodimers and react with an anti-clonotypic antibody and two antibodies directed to the C domain of the TcR.

Guy et al., "Antigen-Specific Helper Function of Cell-Free T Cell Products Bearing TcR $V_\beta 8$ Determinants", *Science*, 244, 1477–1480 (June 1989) report isolating TcRs from the supernatant of cloned T-helper cells. The molecular size of these TcRs was reported to be approximately 500 kD in its native state, which Guy et al. indicated would probably exist in a large complex. It, therefore, appears that these probably represent transmembrane TcRs in micelles. Therefore, Guy et al.'s TcRs are not truly soluble, and accordingly, are quite different than the present invention.

Goverman et al., *Cell,* 60, 929–939 (March 1990) report constructing polymeric receptor chains in which an immunoglobulin heavy chain variable region from a phosphorylcholine-specific antibody was substituted for a TcR α and β variable regions. The modified receptor chain constructs were transfected into the mouse T-cell lymphoma EL4, and drug resistant clones were isolated. Goverman et al., however, utilize this construction to investigate the structure of antibodies rather than producing soluble TcRs.

In conclusion, none of the related art describe the production of soluble TcRs which have the same structure and molecular weight of the soluble TcRs of the present invention. In addition, the process for producing the soluble TcRs of the present invention is quite different than any of the techniques reported in these publications.

SUMMARY OF THE INVENTION

These and other purposes are achieved by the present invention which provides soluble recombinant α/β T-cell receptors for diagnostic and therapeutic use. Specifically, the invention relates to soluble TcR molecules and a process to produce these soluble counterparts of membrane bound TcR molecules. The process to produce these soluble molecules includes replacing the transmembrane domains of the TcR α and β chain cDNAs with a signal for glycosylphosphatidyl inositol (GPI) linkage from the carboxy terminus of the GPI linked protein Thy-1. These chimeric cDNAs are then transferred into an expression vector pFRSVSRα, which contains a strong promoter and a mutant DHFR gene allowing high levels of transcriptional expression and amplification of the gene. These chimeric genes are then cotransfected into a variant of the mouse T-cell lymphoma BW5147, which lacks endogenous TcR genes, and transfectants are selected in methotrexate (a drug for which DHFR gene confers resistance) and screened with antibodies for the TcR. These GPI linked TcR molecules are then solubilized by cleavage with the enzyme phosphatidyl inositol specific phospholipase C (PI-PLC) and purified/concentrated from the supernatant by passage over a TcR reactive antibody affinity column. Using this process, 50 µg of soluble TcR have been produced from $1 \times 10^9$ cells.

For a better understanding of the present invention, reference is made to the following description and Examples taken in conjunction with accompanying figures, the scope of which is pointed out in the appended claims.

BRIEF DESCRIPTION OF DRAWINGS

FIGS. 1A–B shows the construction scheme in accordance with the present invention of TcRα/Thy-1 and TcRβ/Thy-1 chimeric cDNAs. (FIG. 1A) chimeric cDNA constructs (FIG. 1B) junctional sequences αTCR/Thy-1 (SEQ ID NO:1) and βTCR/Thy-1 (SEQ ID NO:2).

FIGS. 4A–B shows two graphs comparing the effects of soluble 2C TcR (FIG. 4A) and soluble D10TcR (FIG. 4B) on P815 cells.

FIG. 5 shows two graphs comparing the effects of soluble D10TcR (Panel A) and soluble 2C TcR (Panel B) on D10 cell proliferation.

FIG. 6A shows GPI-TcR expression after amplification with 50 nM methotrexate. FIG. 6B shows GPI-TcR expression after amplification with 50 µM methotrexate. On both panels, the abscissa is FITC fluorescence from $10^0$ to $10^2$ logarithmic units.

FIGS. 8A–B shows the 2C GPI-TcR transfectant (2G2). FIG. 8C-D shows the D10 GPI-TcR transfectant (1B8).

FIGS. 10A–10B show the analysis of the 2C16 transfectant with the 1B2 antibody. FIGS. 10C–10D show the analysis of the 2C16 transfectant with the H57-597 antibody. FIGS. 10E–10F show the analysis of the AK19 transfectant with the H57-597 antibody.

DETAILED DESCRIPTION OF THE INVENTION

Figure 1A:
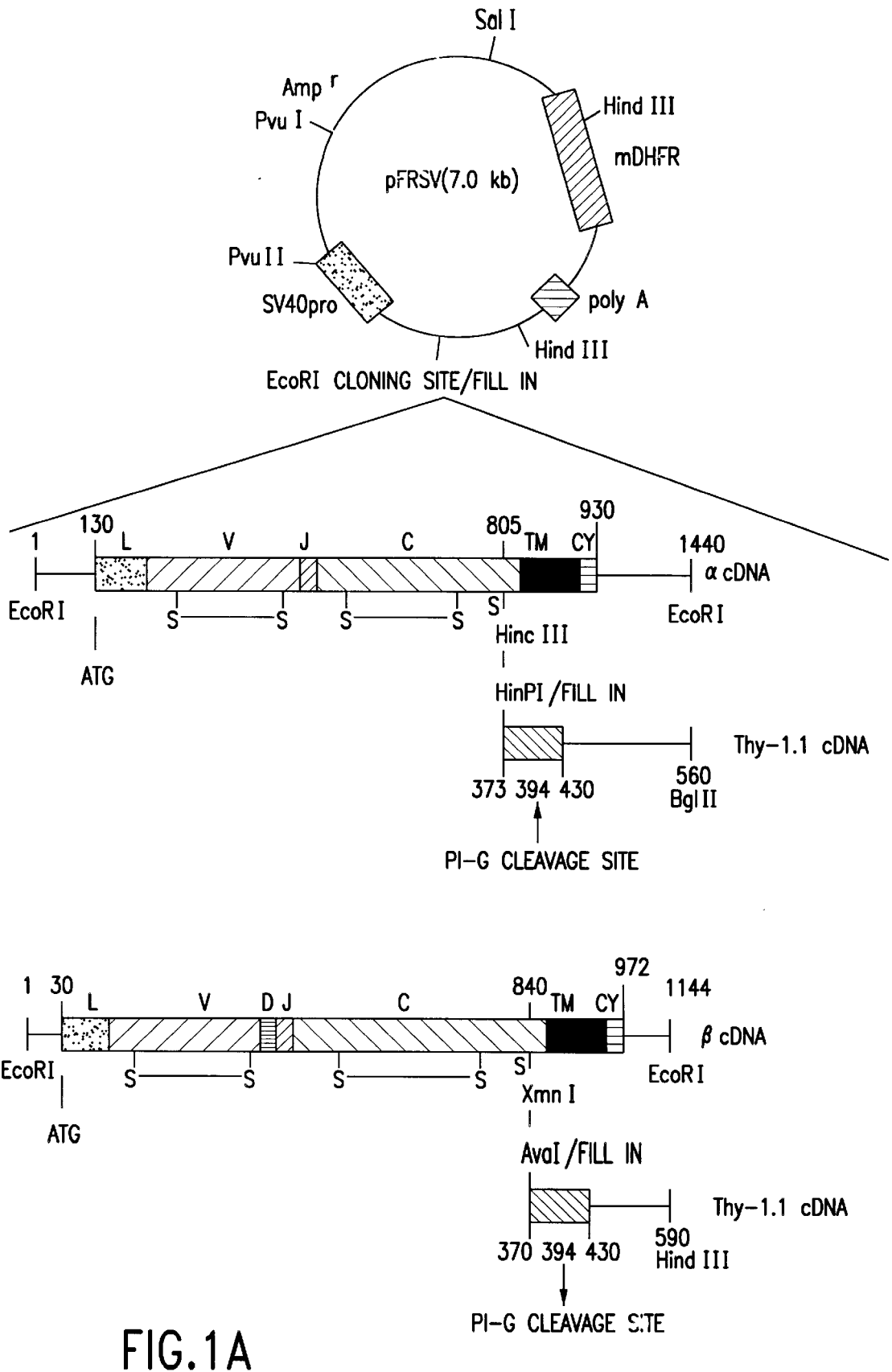

In accordance with the present invention, the inventors have spliced the extracellular domains of the 2C T cell receptor (TcR) to the GPI membrane anchor sequences of Thy-1 and expressed these constructs in the BW5147 T cell lymphoma. The intact GPI anchored form of the T cell receptor so produced is assembled in the native conformation as judged by reactivity with anti-clonotypic, anti-Vβ, and anti-Cβ monoclonal antibodies. It is a disulfide linked heterodimer with an Mr of 95 kDa on SDS-PAGE under nonreducing conditions, and 47 kDa after reduction. The resultant protein can be solubilized by treatment with phosphatidylinositol specific phospholipase C (PI-PLC).

Since CHO is the classical cell line which is used for methotrexate (MTX) selection and amplification, the inventors initially transfected these same cDNA constructs into CHO cells. Preliminary attempts by the inventors to express heterodimeric TcR molecules in CHO cells have failed to produce α/β TcR which express the 1B2 epitope. None of the 29/130 CHO cell transfectants which reacted with the F23.1 antibody by flow cytometry (FCM) analysis in a PI-PLC sensitive fashion also reacted with the 1B2 antibody (data not shown). This 1B2 nonreactive group included several transfectants that expressed high levels of α TcR/Thy-1 mRNA (data shown in FIG. 2C–D shown). Although Davis et al., *Cold Spring Harbor Symp. Quant. Biol., LIV,* 119 (1989), have used CHO cells to produce a GPI linked counterpart of the 2B4 α/β TcR with decay accelerating factor sequences, the results obtained by the inventors show that a T cell specific processing event and/or glycosylation is required to obtain the correctly paired α/βstructure.

The inventors hypothesized that GPI linked molecules might have the advantage of bypassing the requirement of CD3 association with T cell receptor α and β chains for cell surface expression.

The carboxyl terminus of Qa-2 described by Waneck et al., *J. Exp. Med.,* 165, 1358 (1987); decay accelerating factor (DAF) reported by Caras et al., *Science,* 238, 1280 (1987); and Thy-1 reported by Brown et al., *Science,* 245, 1499 (1989) have been successfully used to replace transmembrane anchors with a glycosyl phosphatidylinositol (GPI) membrane anchor. The general strategy used by the inventors in making the present invention is to produce a soluble counterpart of the membrane bound TcR by splicing the extracellular domains of the TcR to the GPI membrane anchor sequences of Thy-1. The greatest problem anticipated was the generation of appropriate α and β chain pairing in GPI forms of TcR molecules. At the time, there were no definitive reports of heterodimers generated using this approach.

To ascertain unambiguously whether correct chain pairing is obtained, the inventors chose a TcR for which an antibody was available that recognizes only the correctly paired structure. The TcR α/β produced by the 2C cytolytic T cell (CTL) clone can be detected using the anti-clonotypic antibody 1B2, the $V_\beta 8$ specific antibody F23.1, or the $C_\beta$ specific antibody H57-597, as discussed by Kranz et al., *Proc. Natl. Acad. Sci. USA,* 81, 7922 (1984); Staerz et al., *J. Immunol.,* 134, 3994 (1985); and Kubo et al., *J. Immunol.,* 142, 2736 (1989). The 2C CTL is alloreactive to the $L^d$ class I molecule, as reported by Kranz et al., *Proc. Natl. Acad. Sci. USA,* 81, 573 (1984).

The inventors' methodology for expressing GPI linked and soluble forms of TcRs should have many applications for α/β and γ/δ TcR structure/function studies. This strategy can be generally used for all TcR since the extracellular portions of the TcR are essentially intact. The fact that this GPI approach should be broadly generalizable contrasts with the fusion of TcR Variable/Junctional (VJ) regions (i.e. the region of the TcR which encodes the properties of antigen specificity and MHC restriction) to immunoglobulin constant regions where appropriate pairing may be VJ region dependent, reported by Traunecker et al., *Immunol. Today,* 10, 29 (1989). In addition, in an effort to bypass the necessity for PI-PLC treatment, the inventors are analyzing transformants of BW5147 class B mutant which secrete GPI linked proteins directly into the supernatant, as reported by Hyman, *Trends Genet.,* 4, 5 (1988). The Inventors are purifying large quantities of this molecule to perform functional studies.

The production of a soluble counterpart of the membrane bound TcR will facilitate a) the determination of its affinity for the different ligands with which it interacts, b) the calculation of the number of ligands per cell with which it interacts, c) its structural characterization by x-ray crystallography, d) the localization of peptide:MHC complex formation within cells, e) the biochemical purification of antigenic peptides or unknown ligands, and f) the specific blockade of particular cell surface TcR in vitro or in vivo for therapeutic purposes or for functional studies.

Soluble TcRs made in accordance to the present invention were compared to membrane bound TcRs in a number of assays.

1. The soluble TcRs reacted with anti-clonotypic antibodies (antibodies which recognize combinatoral determinants comprised of residues of the VJ regions of both the α and β chains on the TcR) indicating that they are paired correctly. Correct association of 2C TcR has been demonstrated by staining with the single available clonotypic antibody, 1B2 and by ELISA on the soluble molecule.

2. Correct association of the D10 TcR has been demonstrated by staining and ELISA with eight clonotypic antibodies.

3. The soluble TcR molecule of the present invention migrated on nonreduced and reduced SDS gels at the expected molecular weight for TcRs (2C TcR); D10 TcR.

4. The soluble TcRs of the present invention specifically inhibit the in vitro alloresponse (i.e. the response to nonself MHC which is responsible for organ graft rejection) of the clone of origin, but not of the irrelevant T-cell clone; see FIGS. 4A–B and 5A–B.

Several modifications may be made to the present invention.

1. PI-PLC is an expensive enzyme. Accordingly, a thrombin site may be inserted into the cDNA sequences used in the present invention and solubilized by treatment with thrombin instead of PI-PLC.

2. Enzyme treatment may be bypassed completely by transferring the existing chimeric cDNA constructs into a variant of the BW5147 T-cell lymphoma called B-mutant which secretes all GPI linked molecules instead of connecting them to the membrane. Alternatively, enzyme treatment may be bypassed by replacing the transmembrane region of the TcR α and β chain cDNAs with the secretory subunit of antibody genes or by inserting a secretory leader sequence and a linker between the variable regions of α and β to produce a single chain antigen binding molecule.

3. It is possible that not all of the molecules are forming disulfide-linked heterodimers. Accordingly, an extra cysteine codons may be inserted into the cDNAs of the present invention.

4. Other types of receptors including γδ and NK cell receptors could also be made soluble using the techniques of the present invention.

There are many applications for soluble T cell receptor molecules of the present invention. The membrane bound T cell receptor is the molecule which is responsible for the T cell's recognition of the antigen for which it is specific. In its soluble form it is analogous to a monoclonal antibody except that it recognizes fragments of peptides associated with MHC molecules while antibodies recognize determinants on a whole protein.

Many autoimmune diseases are mediated by T cells reactive to autoantigens. By cloning these pathogenic T cells, cloning their T cell receptor genes and making these receptors soluble, a number of new and specific treatments for autoimmune diseases can be obtained. First, by injecting the soluble T cell receptor molecules from these clones into patients, the soluble T cell receptor could be therapeutic by a number of mechanisms. These mechanisms include the direct blockade of the pathogenic T cell's ligand, the production of antibodies by patients which are reactive with this T cell receptor that inactivate the pathogenic T cells, and the processing of the soluble TcR as an antigen leading to the production by patients of T cell receptor reactive T cells which downregulate the pathogenic T cells. Second, soluble T cell receptor molecules are easier to raise antibodies against than are their membrane bound counterparts. Antibodies reactive to the T cell receptor of the pathogenic T cells could be administered to the patient to directly inactivate the pathogenic T cells. Finally, soluble T cell receptor molecules from pathogenic T cells may be useful as reagents with which to identify and purify autoantigens which cause autoimmune diseases. Analogues of these autoantigens could then be created which would block the binding of the autoantigen to the MHC molecule preventing activation of the pathogenic T cells.

Soluble T cell receptors may also be applied to prevent the rejection of organ transplants. Since organ rejection results from the alloresponse, which the soluble T cell receptor molecules can inhibit in vitro, direct blockade of the pathogenic T cell's ligand may be possible. In addition, since T cell lymphomas express a single type of T cell receptor, another application of soluble T cell receptors would be to produce soluble T cell receptors from a tumor and inject it as treatment. Furthermore, soluble T cell receptors may be useful to direct the immune response towards protective epitopes in infectious agents. Many diagnostic applications exist in vitro and in vivo if the receptor can be demonstrated to bind to its ligand.

In animal models for autoimmune diseases pathogenic T cell clones do exist. Specifically, in the Non Obese Diabetic (NOD) Mouse model of Type 1 Diabetes, pathogenic islet specific T cell clones are available and their T cell receptor cDNAs have been cloned. By making soluble counterparts of these membrane bound T cell receptors, injecting them into the NOD mice and determining if disease is prevented, the effectiveness of using soluble T cell receptors as therapy for autoimmune diseases can be determined. Likewise, soluble T cell receptor molecules can be used to study the prevention of EAE (an experimental model for multiple sclerosis). To use this approach as a therapy in humans, pathogenic T cells would first be cloned from human subjects. The production of clones from peripheral blood or from diagnostic biopsies is practical. Theoretically, the efficacy of the soluble T cell receptor molecules cloned from these T cells can be determined by their ability to block disease in the patient.

In summary, these soluble receptors may be used therapeutically to isolate and identify natural and artificial ligands and study membrane-bound proteins. Proteins and antibodies to the soluble TcRs may be used in diagnosis and treatment of autoimmune diseases. Additionally, in a model autoimmune system, experimental allergic encephalomyelitis, antibodies directed against TcRs inhibited and even reversed the development of the disease. In addition, the soluble TcRs may be applicable to preventing rejection during organ transplantation and as therapy to prevent autoimmune disease.

EXAMPLES

1. Materials and Methods a) Plasmid Constructs

The 3' Hinc II-EcoR I restriction fragment from the TcR α cDNA was replaced by the 270-bp HinP I-Bgl II fragment from the Thy-1.1 cDNA. Similarly, the Xmn I-EcoR I fragment from the TcR β cDNA was replaced by the 160 bp Ava I-Hind III fragment of the Thy-1.1 cDNA. Finally, the EcoR I-Bgl II fragment of a TcR/Thy-1 and the EcoR I-Hind III fragment of b TcR/Thy-1 were transferred into the EcoR I cloning site of pFRSV. The nucleotide sequences of the TcR/Thy-1 junctions (SEQ ID NO:1; SEQ ID NO:2) were confirmed by dideoxy sequencing methods. The α TcR chain cDNA(p2C1B2-A-4) and the β TcR chain cDNA(p2C1B2-B-18) were obtained from Dr. S. Tonegawa. The Thy-1.1 cDNA was obtained from Dr. I. Lemischka. The expression vector pFRSV was obtained from Dr. A. Horwich.

b) Transfections

The pFRSV(TcRα/Thy-1) and the pFRSV(TcRβ/Thy-1) constructs described above were linearized with Sal I and cotransfected (using 50 μg of each plasmid) into the BW5147 thymoma by electroporation (320V, 960 μF) using a BIORAD Gene Pulse electroporation device (Richmond, Calif.). Methotrexate (MTX)-resistant clones were selected at 50 nM MTX and, at alternate passages, the MTX levels were increased to a level of 50 μM MTX. The MTX-resistant clones were then screened by staining with 1B2 and F23.1 monoclonal antibodies followed by FCM analysis and the double transfectant 3A3 was further selected to a final concentration of 200 μM MTX.

c) Antibody Staining and Flow Cytometric (FCM) Analysis

Cells were incubated with F23.1 or 1B2 antibody for 20 minutes followed by 20 minutes with FITC-labeled goat anti-mouse antibody. Background (BKG) refers to staining of cells only with FITC-labeled goat anti-mouse antibody. Three washes were performed following incubation with each serological reagent. After staining, the cells were fixed in 1% paraformaldehyde and analyzed by flow cytometry (FCM), i.e., FACS analysis. The 2C CTL clone and the 1B2 clonotypic antibody specific for its TcR were kindly provided by Dr. D. Kranz. The F23.1 $V_{62}8$ specific antibody was the gift of Dr. C. Janeway, Jr.

d) Phosphatidyl Inositol-Specific Phospholipase C PI-PLC) Treatment

3A3 transfectants ($2 \times 10^7$) were incubated in 500 ml of RPMI (Gibco) medium containing 0.25 units of PI-PLC (ICN Biochemicals, Costa Mesa, Calif.) at 37° C. for 1 hour and pelleted by centrifugation for 5 min at 3000 rpm in a microcentrifuge. The supernatant (SN) collected from the pellet is referred to as PI-PLC (SN) and contains the soluble TcRs of the present invention.

e) Iodination and Immunoprecipitation

The 2C CTL clone ($2\times10^7$ cells) and the 3A3 αTcR/Thy-1:βTcR/Thy-1 BW5147 transfectant ($2\times10^7$ cells) were surface iodinated using the lactoperoxidase method described by Cone et al., *Biochem. J.*, 104, 435 (1974). The labeled cells were washed five times with PBS. After washing, the labeled 2C CTL were lysed on ice in 500 μl of lysis buffer (0.5% NP40, 1 mM EDTA, 1 mM iodoacetamide, 1 mM PMSF, 1X PBS). In contrast, the labeled 3A3 transfectants were incubated in 500 ml of RPMI medium containing 0.25 units of PI-PLC (ICN Biochemicals) at 37° C. for 1 hour and pelleted by centrifugation for 5 min at 3000 rpm in a microcentrifuge. Both the 2C lysate and the 3A3 PI-PLC SN were then microcentrifuged for an additional 30 minutes at 12,000 rpm. Aliquots containing $1\times10^7$ cpm were precleared in the presence of 0.5% BSA by incubation on ice with 5 ml of 3G5F12 ascites fluid (an irrelevant antibody) followed by incubation with 50 μl of a 50% slurry of protein G agarose (Genex Corporation, Gaithersburg, Md.). The agarose beads were removed by centrifugation. An additional 50 μl of agarose beads was added for 30 minutes on ice and again removed by centrifugation. Aliquots of the precleared SN were then incubated overnight on ice in the presence of 3 μl of 1B2, F23.1 or 3G5F12 ascites fluid. The specific immune precipitates were then recovered by addition of 50 μl of a 50% slurry of protein G agarose for 30 minutes on ice followed by centrifugation. The beads were washed 4 times with washing buffer (0.1% NP40, 1 mM EDTA, 1 mM iodoacetamide, 1 mM PMSF, 1X PBS). Subsequently, the proteins were eluted from the beads by boiling for 5 minutes in 30 μl of SDS loading buffer (4% SDS, 62.5 mM Tris-HCl pH 6.8, 40% glycerol, 0.02% Bromophenol blue) in the absence (for nonreduced gels) or the presence (for reduced gels) of 5% 2-mercaptoethanol (2-ME) and separated on 10% polyacrylamide SDS gels. The control lanes were treated with an ascites preparation, 3G4F12, that is reactive with a Leshmania flagellar protein and was kindly provided by Dr. D. McMahon-Pratt (Yale Medical School).

Example 1

Construction of Chimeric TcR α/β/Thy-1 cDNAs

The strategy to construct chimeric TcR/Thy-1 α and β chain cDNAs is diagrammed in FIGS. 1A–B. FIG. 1A shows the chimeric cDNA constructs, and FIG. 1B shows the junctional sequences αTCR/Thy-1 (SEQ ID NO:1) and βTCR/Thy-1 (SEQ ID NO:2). The particular TcR/Thy-1 junctions were chosen to retain the cysteines in the TcR constant (C) region which contribute the interchain disulfide bonds involved in α and β chain pairing and to maintain the distance between these cysteines of the α chain and the β chain and the site of GPI attachment to the cell surface. There are restriction sites in the α(Hinc II) and β(Xmn I) TcR cDNAs located between the last cysteine residue in the C region and the transmembrane domain. Cleavage of the Thy-1 cDNA at either Ava I or HinP I and blunting the restriction site using the Klenow DNA Polymerase results in a junction that satisfies the above criteria. The sites chosen in the TcR cDNA result in the removal of about 15 amino acids on the extracellular side of the transmembrane domain, and their replacement with about 20 amino acid residues of Thy-1 plus the GPI anchor. Finally, to achieve high levels of expression the pFRSV DHFR expression vector was used, which has the SV40 early promoter and enhancer for expression and contains a mutant DHFR gene that permits methotrexate selection and gene amplification in DHFR$^+$ as well as in DHFR$^-$ recipient cells. These constructs were subsequently expressed in BW5147 mouse thymoma cells, as described by Ralph, *Immunol.*, 110, 1470 (1973).

Example 2

The Chimeric TcRα/β/Thy-1 Molecules are Folded in their Native Conformation and are Solubilized by PI-PLC Treatment The chimeric cDNAs in the pFRSV expression vector were co-transfected into BW5147 cells by electroporation and selected initially in 50 nM methotrexate (MTX). Sixty transformants were analyzed at this stage of drug selection for cell surface expression by FCM analysis using the F23.1 antibody. No obvious expression was detected. Subsequently, the clones were selected in increasing levels of MTX up to 50 μM MTX to achieve DHFR mediated gene amplification. Analysis of the 60 transformants selected at 50 μM MTX revealed 12 that expressed significant levels of TcR detectable with F23.1. These 12 transfectants were then screened with the 1B2 antibody and 5 transfectants were positive.

Figure 2A:
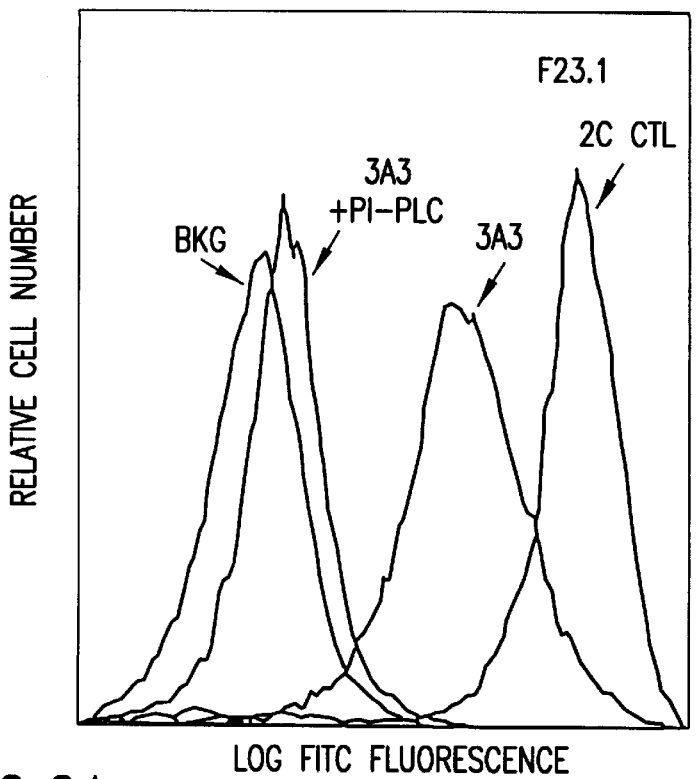
FIGS. 2A–B shows two graphs plotting the expression of GPI-anchored 2C TcR α/β in BW5147 thymoma cells analyzed by FCM (i.e., FACS analysis) after staining with the anti-$V_{62}$8 monoclonal antibody (mAb) F23.1 (FIG. 2A); and the anti-clonotypic mAb 1B2 (FIG. 2B) followed by FITC goat anti-mouse antibody. Background (BKG) refers to staining of 3A3 cells only with FITC-labeled goat anti-mouse antibody. The treatment with PI-PLC was as described in the Materials and Methods section of the Examples.
Figure 2B:
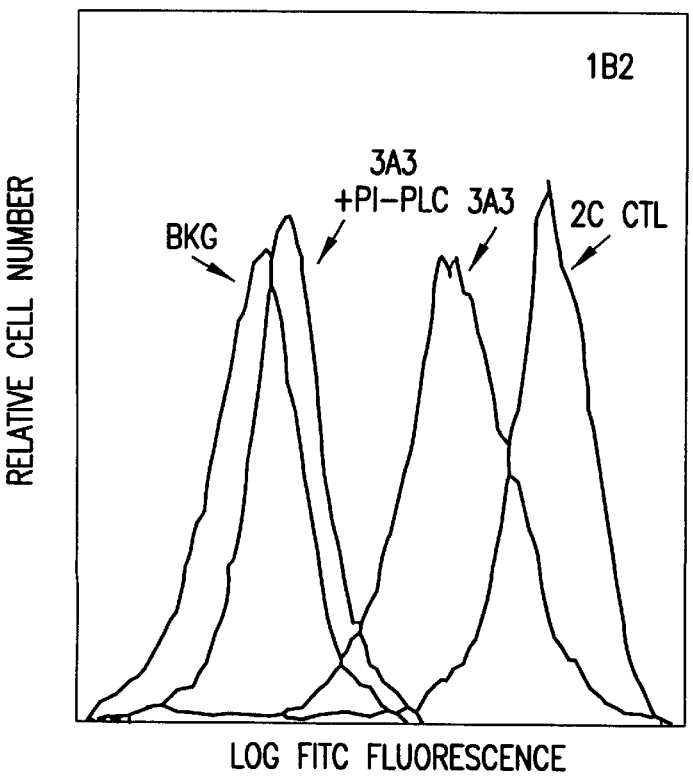
Figure 2C:
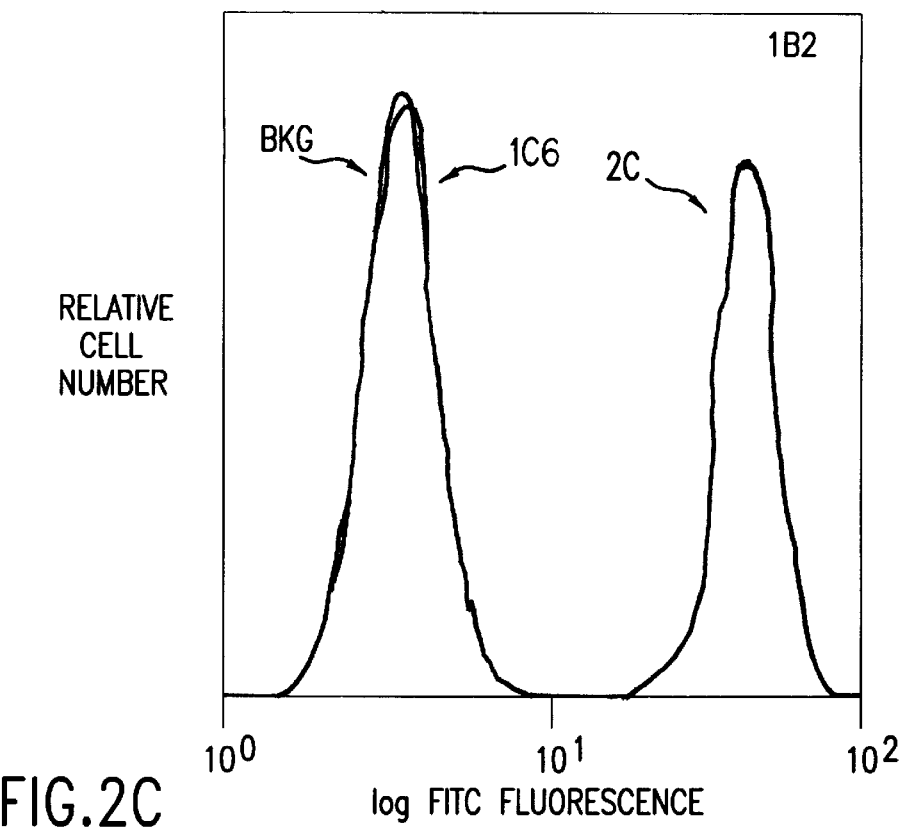
FIGS. 2C–D shows two graphs plotting the expression of GPI-anchored 2C TcR α/β in CHO cells analyzed by FCM: (1) after staining with the anti-clonotypic monoclonal antibody (mAb) 1B2 followed by FITC goat anti-mouse antibody (FIG. 2C); and (2) after staining with the anti-$V_β8$ Mab F23.1 followed by FITC goat antimouse antibody (FIG. 2D).
Figure 2D:
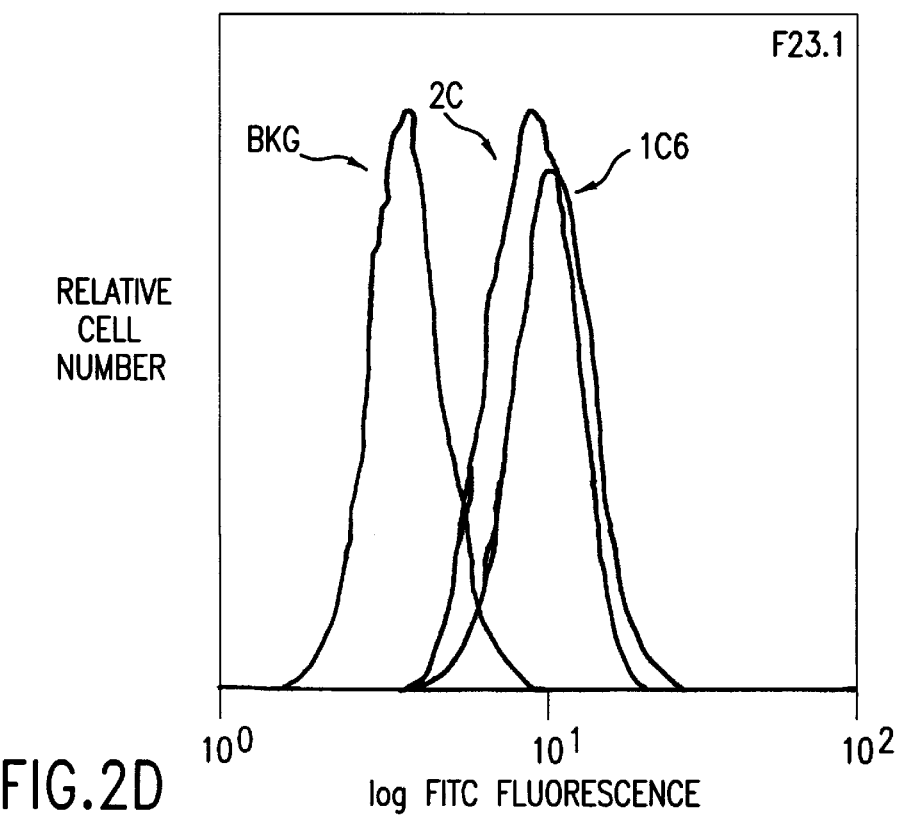

The expression of one clone (3A3), which was further selected at 200 μM MTX, is analyzed in FIGS. 2A–B. The 2C cells and the 3A3 cells express receptor that is detected by both the F23.1 (FIG. 1A) and the 1B2 (FIG. 1B) monoclonal antibodies. This receptor is also detected with the H57-597 $C_\beta$ reactive monoclonal antibody (data not shown). Thus, as judged by reactivity with the clonotypic mAb 1B2, the chimeric TcR α/β/Thy-1 molecule is folded in its native conformation.

The TcR expressed by these cells was then examined for sensitivity to PI-PLC. The levels of F23.1 and 1B2 staining of the 3A3 cells are dramatically reduced after PI-PLC treatment (FIGS. 2A–B) and in some experiments the TcR was completely removed by PI-PLC treatment (data not shown). The 3A3 cells do not express CD3 on the cell surface as judged by lack of reactivity with the 2C11 and the 29B mAbs (data not shown) tested as described by Portoles et al., *J. Immunol.*, 142, 4169 (1989); and Leo et al., *Proc. Natl. Acad. Sci. USA*, 84, 1374 (1987). Single transfectants expressing only the TcR β were also sensitive to treatment with PI-PLC (data not shown).

Example 2A

Chimeric TcRα/β Thy-1 Molecules Expressed by transformed CHO Cells Lack the Native Conformation of a T Cell Receptor The chimeric cDNAs in the pFRSV expression vector were also cotransfected into CHO cells and selected initially with 200 nM MTX. Selection was then continued at alternate passages in ten-fold increments to 200 μm MTX. This experiment was also repeated utilizing the chimeric CDNA constructs in a pFRSV-SR expression vector. All clones selected at 200 μm and 200 nm MTX were stained with F23.1 and 1B2 Mabs. and analyzed by FCM analysis.

No staining was observed with either the F23.1 or 1B2 antibody for the clones selected at 200 μM MTX. At 200 μM MTX, 29 out of 130 CHO transfectants in the first experiment and 24 out of 25 CHO transfectants in the second experiment (pFRSV-SR expression vector) reacted with the F23.1 antibody. However, none of these 59 (29+24) CHO transfectants reacted with the 1B2 antibody.

The analysis of one clone 1C6, which is representative of all 53 clones that reacted with the F23.1 antibody, is shown in FIGS. 2C–D. The FIG. 2C displays the analysis with the 1B2 antibody. The peak for 1C6 clone overlaps the background peak, which is considered a negative control. This overlap of the peaks indicates that binding with the 1B2 antibody did not occur. FIG. 2D displays the analysis with the F23.1 antibody. The 1C6 peak overlaps the 2C peak, which is a positive control. This overlap indicates that binding with the F23.1 antibody did occur. By failing to bind to the 1B2 antibody, it will be apparent to one skilled in the art that the expressed TcRs failed to produce the 1B2 epitope and, therefore, are not folded in a native conformation.

Example 3

The Chimeric TcR α/β/Thy-1 Molecules are Disulfide Linked Heterodimers

Figure 3A:
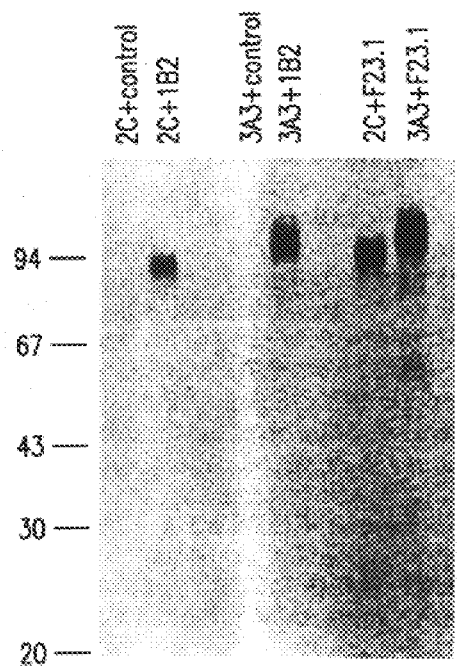
FIGS. 3A–B shows two photographs of SDS polyacrylamide gel electrophoretic analysis of iodinated transmembrane and soluble α/β T cell receptor molecules. Transmembrane (2C) and Phosphatidylinositol-specific phospholipase C (PI-PLC) released Glycosyl phosphatidylinositol (GPI)-linked (3A3) TcR α/β were immunoprecipitated either with the 1B2 anti-clonotypic antibody, the F23.1 anti-$V_β8$ antibody or an irrelevant control antibody. Nonreduced samples are shown in FIG.3A and reduced samples are shown in FIG. 3B.
Figure 3B:
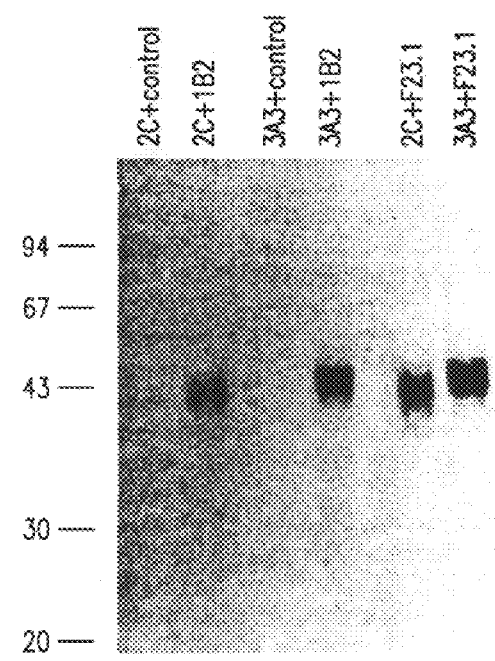

Further proof that the GPI linked TcR of the present invention expressed by the 3A3 transfectant represents the correctly paired structure was obtained by analyzing for the presence of the disulfide linkage between the α and β chains. Proteins on the cell surface of the 3A3 cells and the 2C CTL clone were labeled with $^{125}$I using lactoperoxidase. The 3A3 cells were treated with PI-PLC to solubilize the TcR molecules into the RPMI medium to obtain the soluble TcRs of the present invention. The 2C cells were solubilized in a nonionic detergent solution. These preparations were precleared with an irrelevant antibody and precipitated in the presence of the 1B2 or F23.1 antibodies. The samples were then fractionated on a 10% SDS-PAGE gel with or without 2-mercaptoethanol in the sample buffer (FIGS. 3A–B). As evident in FIG. 3A, the transmembrane 2C TcR migrates at 90 kDa and the PI-PLC released form expressed by 3A3 migrates at 95 kDa. The higher mobility of GPI released proteins has been previously observed, as reported by Eteges et al., *EMBO J.*, 5, 597 (1986). In FIG. 3B, the 2C TcR migrates with a mol. mass of 45 kDa and the 3A3 form migrates at a slightly higher mol. mass. Thus, the PI-PLC solubilized TcR of the present invention is a disulfide linked dimer which retains its native conformation, as judged by reactivity with the 1B2 anti-clonotypic antibody and migrates at the expected molecular weight for a fully processed α/β T cell receptor.

Example 4

Blocking of the 2C CTL Response to P815

The 2C CTL clone killing of its $L^d$ expressing target P815 was studied by chromium release in the presence of the soluble TcR of the present invention. E:T is the ratio of 2C CTL cells to P815 targets. FIGS. 4A–B shows two graphs comparing the effects of soluble 2C TcR of the present invention (FIG. 4A) and soluble D10 TcR (FIG. 4B) on P815 cells.

Example 5

Blocking of the D10 I-$A^b$ Alloresponse

The proliferative response of D10 cells was studied after exposure of the APC's to soluble TcR and fixation. FIG. 5 shows two graphs comparing the effects of soluble D10 TcR (Panel A) and soluble 2C TcR of the present invention on D10 cell proliferation.

Example 6

Increasing the Cell Surface Expression of GPI-TcR Molecules

Figure 6A:
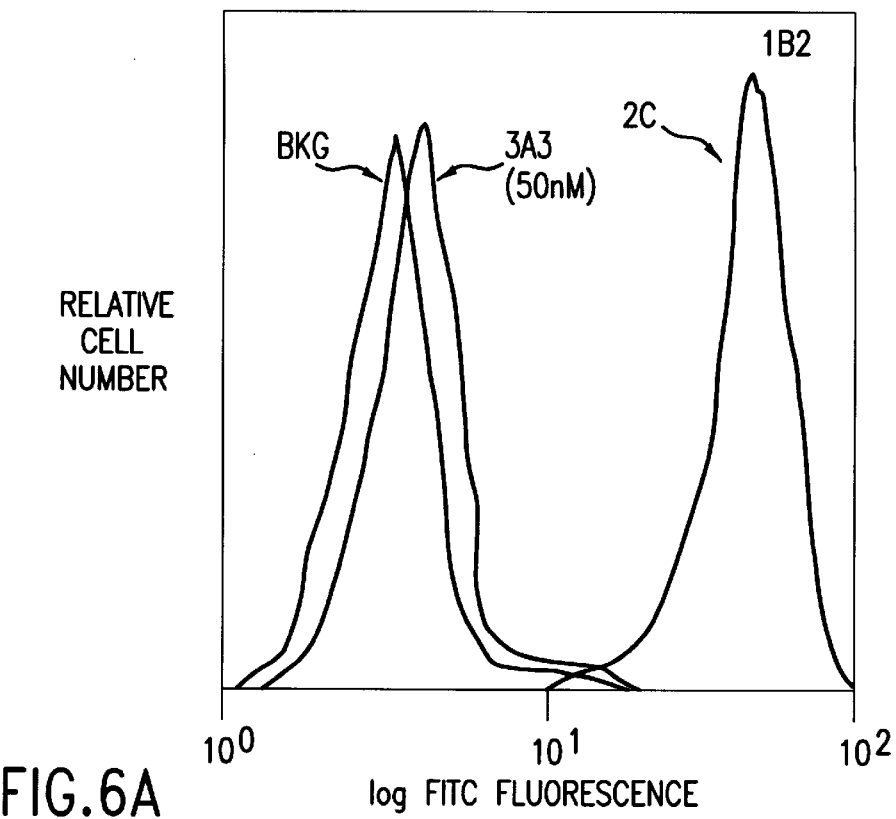
FIGS. 6A–B shows the effect of methotrexate amplification on GPI-TcR expression in BW5147 cells (3A3) as detected by FACS analysis with the 1B2 clonotypic antibody.
Figure 6B:
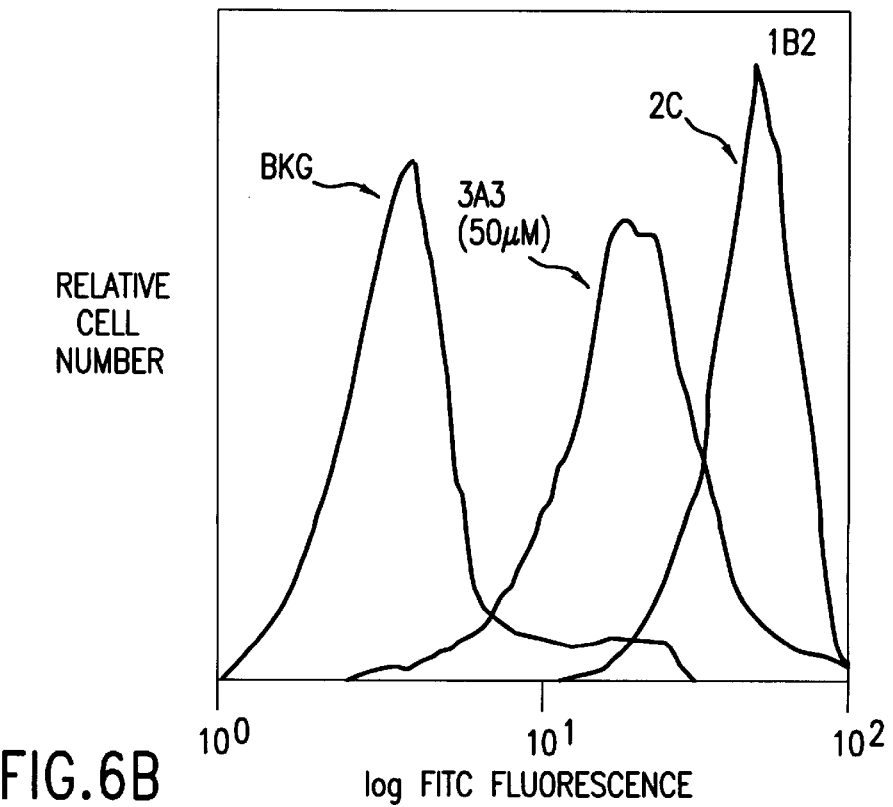

In order to maximize the number of GPI-linked TcR molecules expressed per cell, a method of quantifying their production was first developed. The relative amount of TcR molecules per cell was monitored using the shift in mean fluorescent intensity by FACS analysis. This shift is determined by subtracting the background staining by the FITC labelled secondary antibody alone from the staining which occurs in the presence of primary anti-TcR antibody. The shift in mean fluorescent intensity upon FACS analysis of the αβ TcR/Thy-1 pFRSV transfectant 3A3 fully amplified at 500 μM methotrexate with the 1B2 clonotypic antibody is 0.7 logarithmic units, a shift which is slightly less than the 0.9 logarithmic unit shift exhibited by the 2C clone (FIGS. 7A–K). Furthermore, this shift in fluorescent intensity was significantly greater (by 0.6 logarithmic units) than that exhibited by this transfectant upon initial selection at 50 nM methotrexate (FIGS. 6A–B). Therefore, the level of expression observed with pFRSV was due primarily to DHFR mediated gene amplification.

The possibility existed that the endogenous transmembrane β chain of BW5147 was competing with the GPI form of the 2C β chain (Vβ8) for a T cell specific processing event. The BW5147 cell line expresses an inframe mRNA containing Vβ1 and the resulting protein is retained in the endoplasmic reticulum (Lee and Davis, 1988). Consequently, we selected a derivative of BW5147 (designated 4G4) that lacks expression of endogenous α and β mRNA to be the recipient cell for our chimeric expression constructs (White, et al., "Two Better Cell Lines For Making Hybridomas Expressing Specific T Cell Receptors", *J. Immunol.*, 143, 1822–1825 (1989).

The SRα vector contains a strong promoter for expression in T cells (Takebe, et al., "SRα Promoter: An Efficient and Versatile Mammalian cDNA Expression System Composed of the Simian Virus 40 Early Promoter and the R-U5 Segment of Human T Cell Leukemia Virus Type I Long Terminal Repeat", *Molec. Cell. Biol.*, 8, 466–472 (1988). Comprised of the SV40 promoter in conjunction with the strong HTLV-1 enhancer, the SRα promoter is 120-fold better than the SV40 promoter alone at driving expression of the CAT reporter gene in the human CD3+ T cell lymphoma line Jurkat (Takebe, et al., "SRα Promoter: An Efficient and Versatile Mammalian cDNA Expression System Composed of the Simian Virus 40 Early Promoter and the R-U5 Segment of Human T Cell Leukemia Virus Type I Long Terminal Repeat", *Molec. Cell. Biol.*, 8, 466–472 (1988)). The α and β TcR/Thy-1 chimeric genes were transferred into the pSRα expression vector by blunt-end ligation and the resulting expression constructs were cotransfected into 4G4 with the pSV2Neo plasmid. The pSV2Neo plasmid encodes the resistance gene for the drug G418 and is necessary because the SRα expression vector does not encode a selectable marker.

Figure 7A:
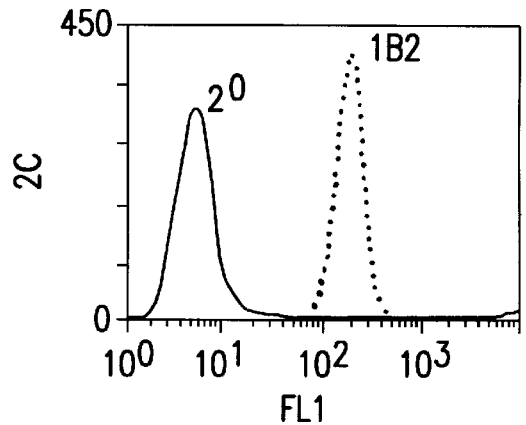
FIGS. 7A–K show 2C GPI-TcR expression with the pFRSV, pSRα and pFRSV-SRα expression vectors, as detected by FACS analysis. Notations in the left column indicate the cells stained: 2C clone, 3A3 (pFRSV) GPI-TcR transfectant of BW5147 at 500 µM MTX, 2G2 (pSRα) GPI-TcR transfectant of 4G4, 2C16 (pFRSV-SRα) GPI-TcR transfectant of BW5147 at 50 nM MTX, 2C16 (pFRSV-SRα) driven GPI-TcR transfectant of BW5147 at 500 µM MTX, and 2C16 (pFRSV-SRα) GPI-TcR transfectant of BW5147 at 500 µM MTX+PI-PLC. Notations in the first row or inside the FACS plots indicate that the cells were stained with 1B2 antibody+FITC conjugated goat anti-mouse secondary (1B2) or with FITC conjugated goat anti-mouse secondary alone ($2°$).

Selection in G418 containing medium yielded seven drug resistant cell clones, two of which reacted with the 1B2 clonotypic antibody. One of these 1B2 reactive transfectants (2G2) was selected for further study. The shift in mean fluorescent intensity upon FACS analysis of 2G2 with the 1B2 clonotypic antibody was 1.0 logarithmic units (FIG. 7A). This shift in mean fluorescent intensity is 0.3 logarithmic units greater than that achieved with the fully amplified FRSV expression vector and is equivalent to the shift observed with 2C. Thus, the SRα expression system in conjunction with the 4G4 cell line resulted in high level expression of GPI-linked TcR molecules in the absence of methotrexate induced gene amplification.

Scatchard analysis of iodinated 1B2 antibody binding to the 2G2 transfectant indicates that there are $1.3 \times 10^5$ molecules per cell (FIGS. 8A–D). The theoretical amount of soluble TcR molecules present in a given number of cells could be calculated by multiplying the number of cells by the number of TcR molecules per cell and using Avogadro's number and the molecular weight of the TcR to convert this number to grams of protein. Calculation of the theoretical amount of soluble TcR molecules present in $1\times10^9$ 2G2 cells yields 21.6 µg.

Example 7

Construction of and Expresion with the pFRSV-SRα Vector

Figure 9:
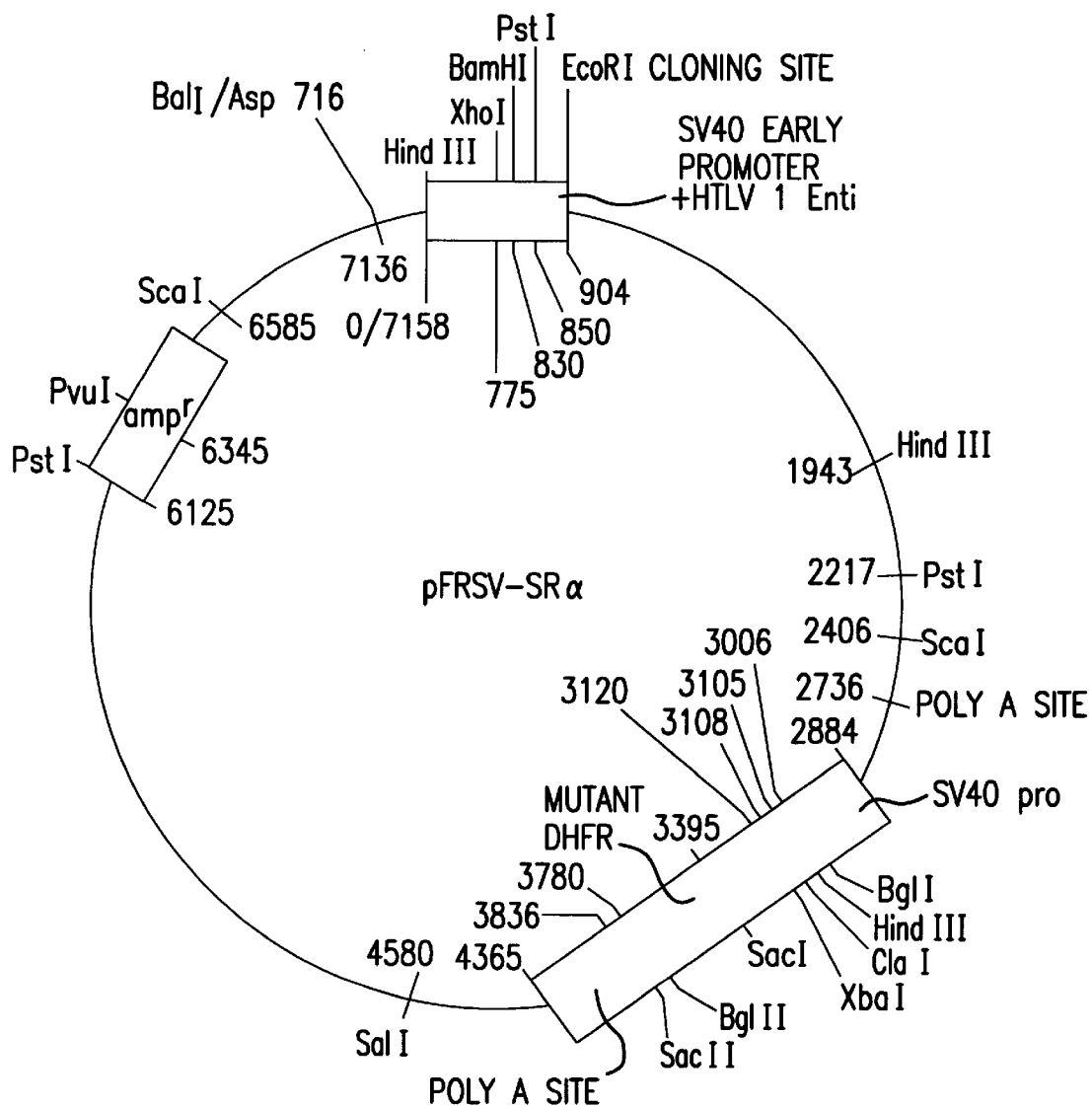
FIG. 9 shows a restriction map of the pFRSV-SRα expression vector. The Sal I-EcoRI fragment containing the SV40 promoter of pFRSV was replaced with the Asp 718-EcoRI fragment containing the SV40 early promoter and the HTLV 1 enhancer of SRα. This vector uses the SV40 promoter and the HTLV 1 enhancer as well as a mutant DHFR gene which allows methotrexate selection and amplification in DHFR positive as well as DHFR negative cell lines. The vector is 7155 bases total and map position 1 indicates the 5' end of the SV40 early promoter.

Reasonably high cell surface expression levels were obtained with the SRα promoter in the absence of methotrexate mediated gene amplification. In addition, the mutant DHFR gene in pFRSV had been used both to select transfectants and to amplify their cell surface expression levels of GPI-linked TcR at least ten-fold. We reasoned that these two components could be combined to create a strong eukaryotic expression system. In order to increase the cell expression levels of GPI-linked TcR molecules, the promoter of the pFRSV plasmid (Sal I-Eco RI) was replaced with the strong promoter region of the pSRα plasmid (Asp 718-Eco RI) to create pFRSV-SRα expression vector shown in FIG. 9.

The α/Thy-1 and β/Thy-1 chimeric cDNAs were blunt-end ligated into the EcoRI cloning site of the pFRSV-SRα expression vector and these expression constructs were cotransfected into BW5147 following the procedure of Example 1. BW5147 cells were selected as recipient cells because they had produced methotrexate selectable and amplifiable GPI-TcR expression in previous experiments.

Figure 7B:
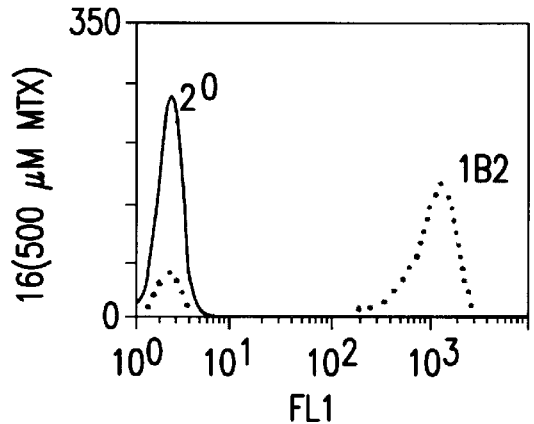
Figure 7C:
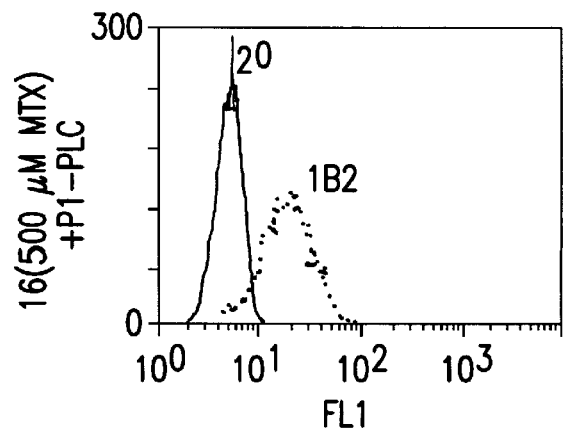
Figure 7D:
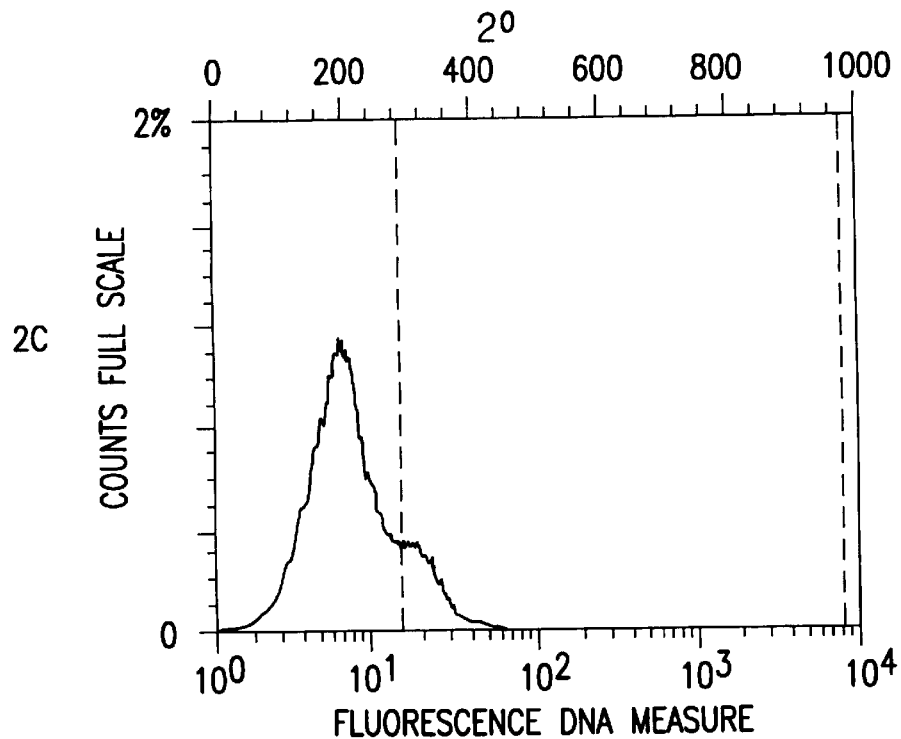
Figure 7E:
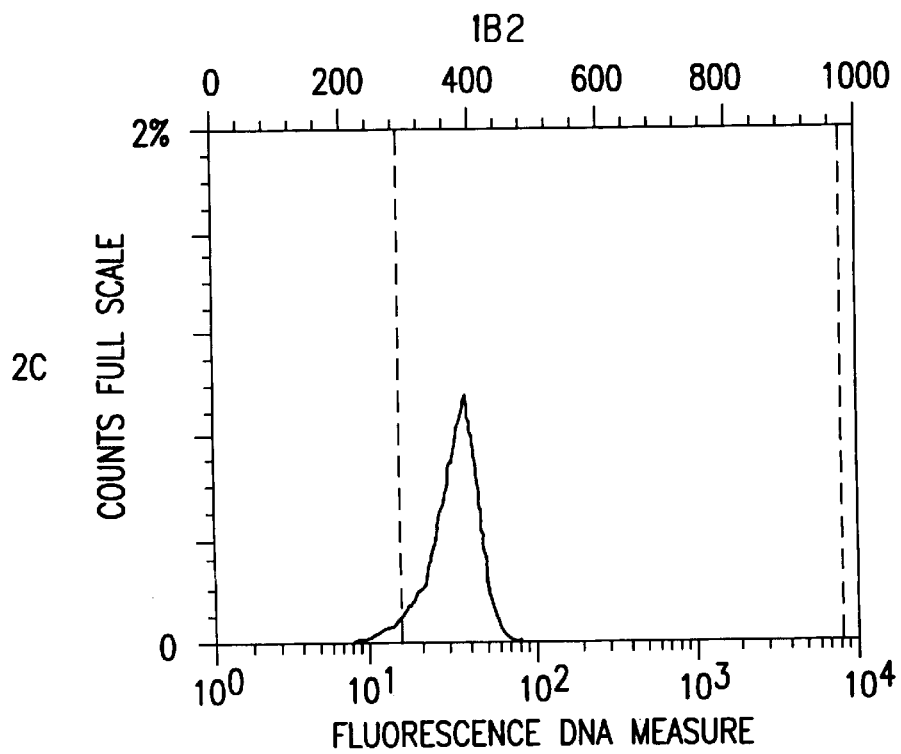
Figure 7F:
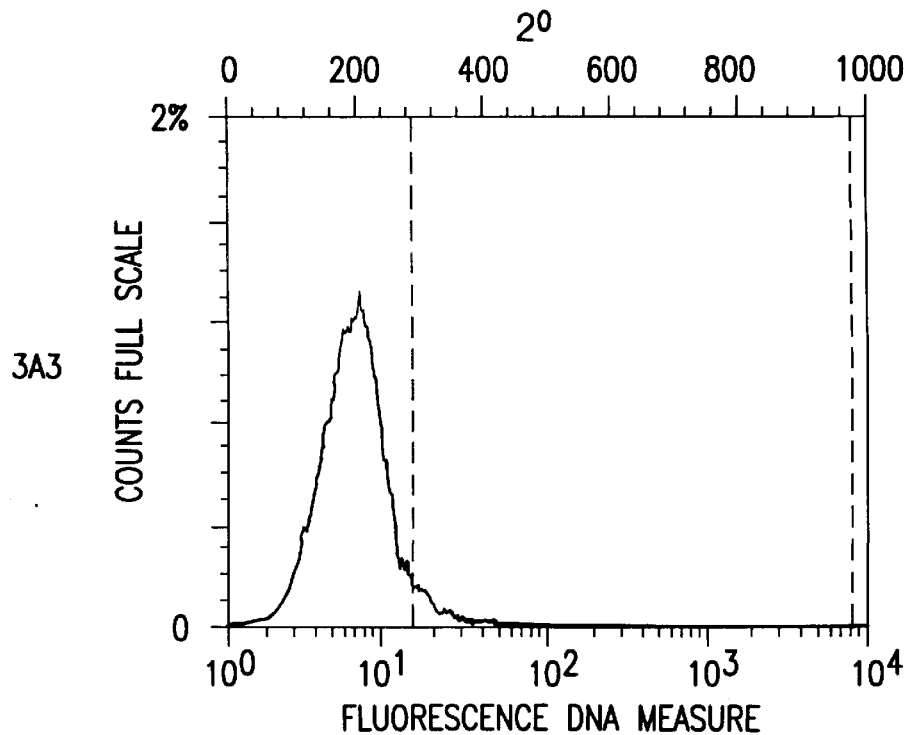
Figure 7G:
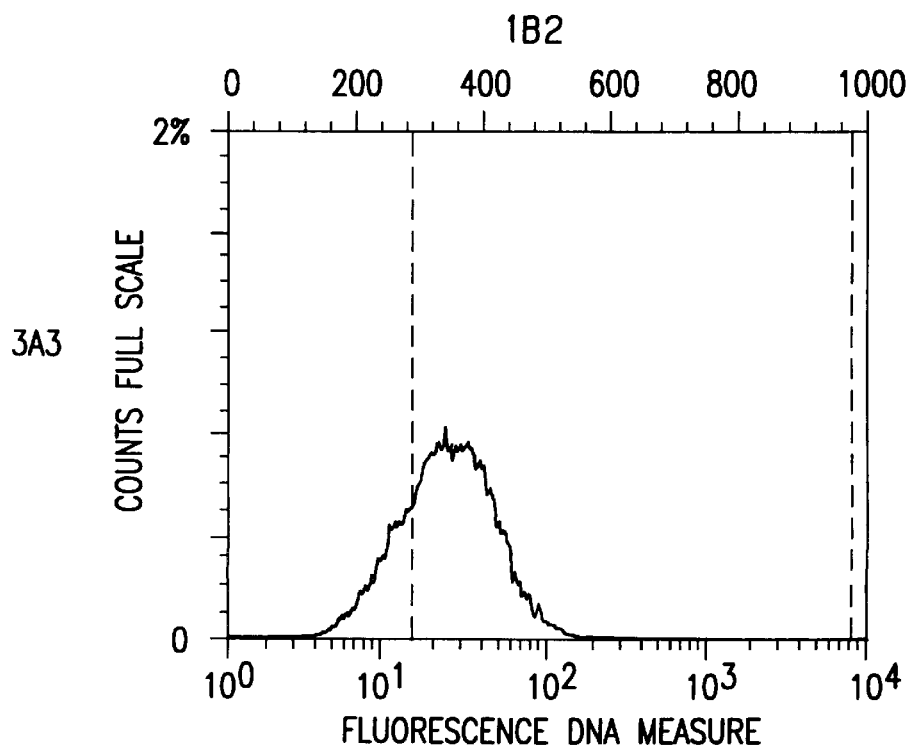
Figure 7H:
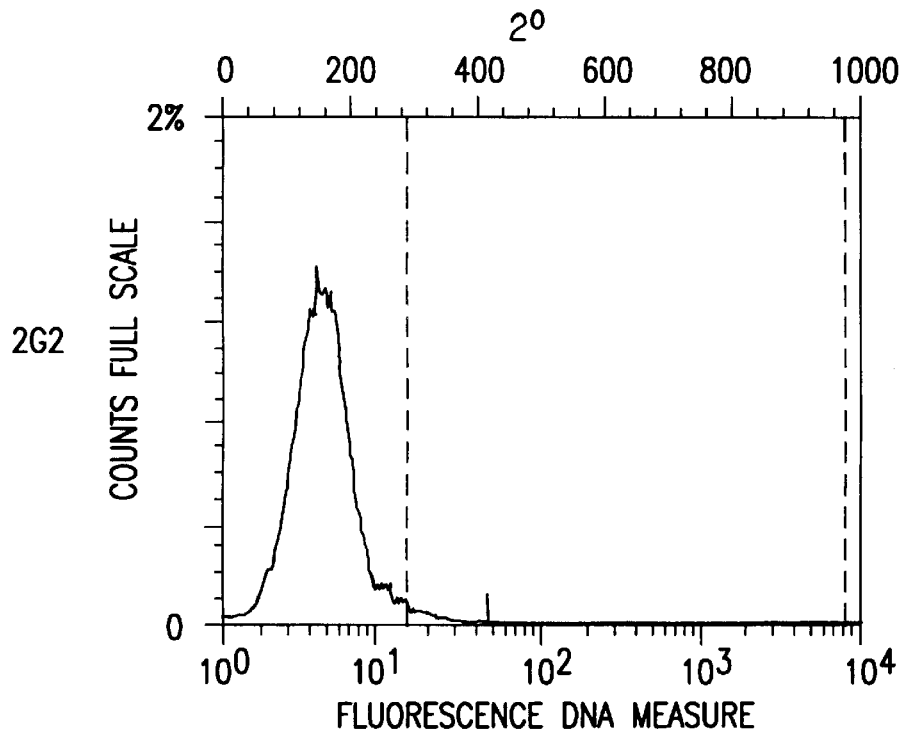
Figure 7I:
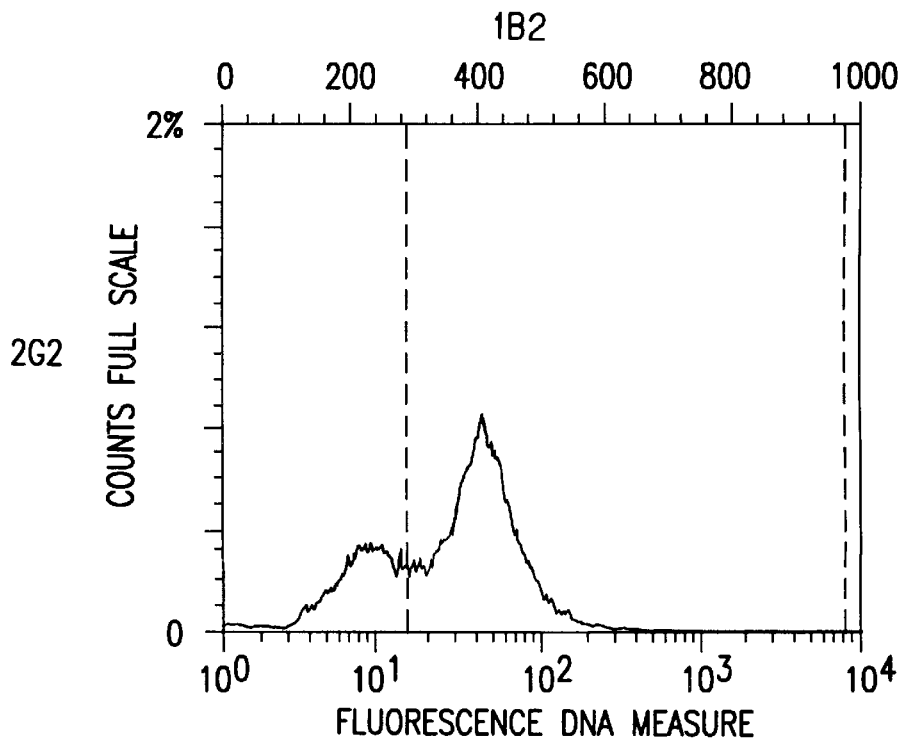
Figure 7J:
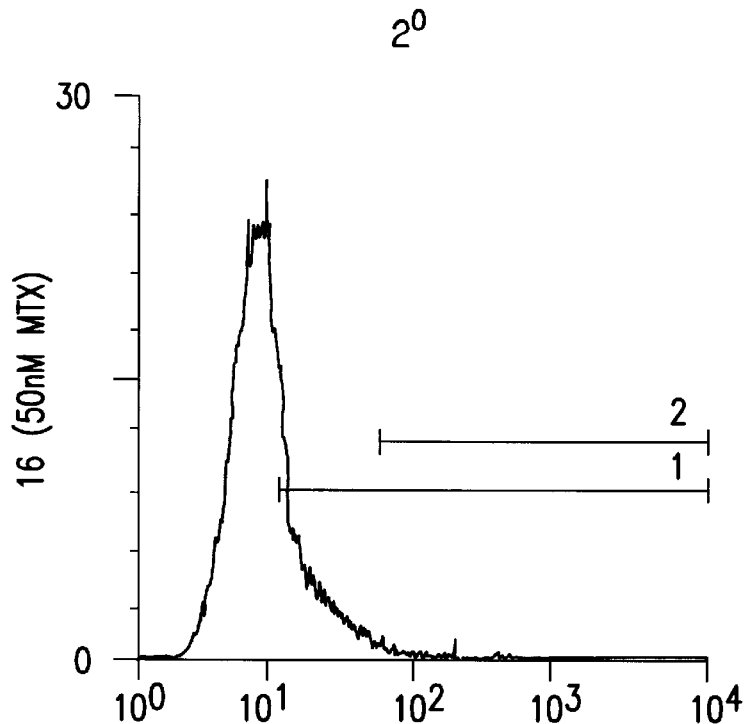
Figure 7K:
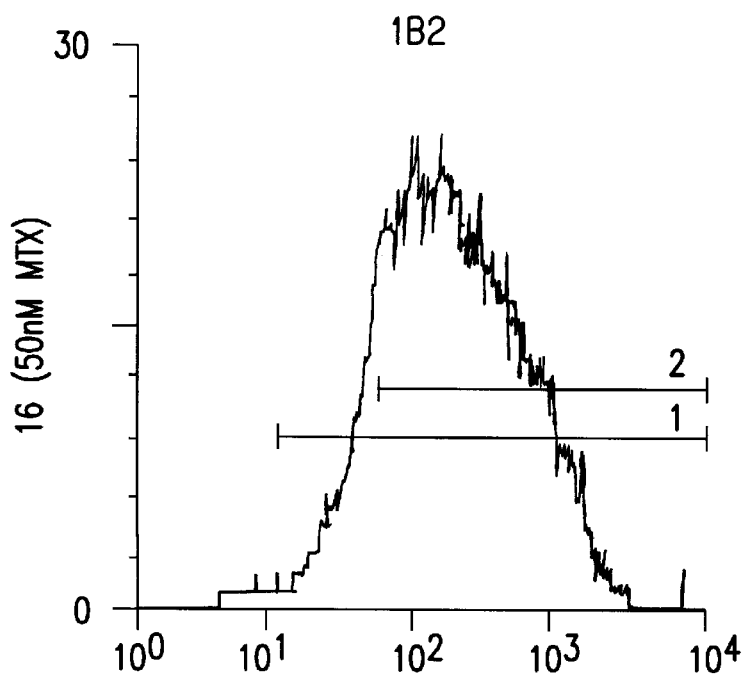
Figure 8A:
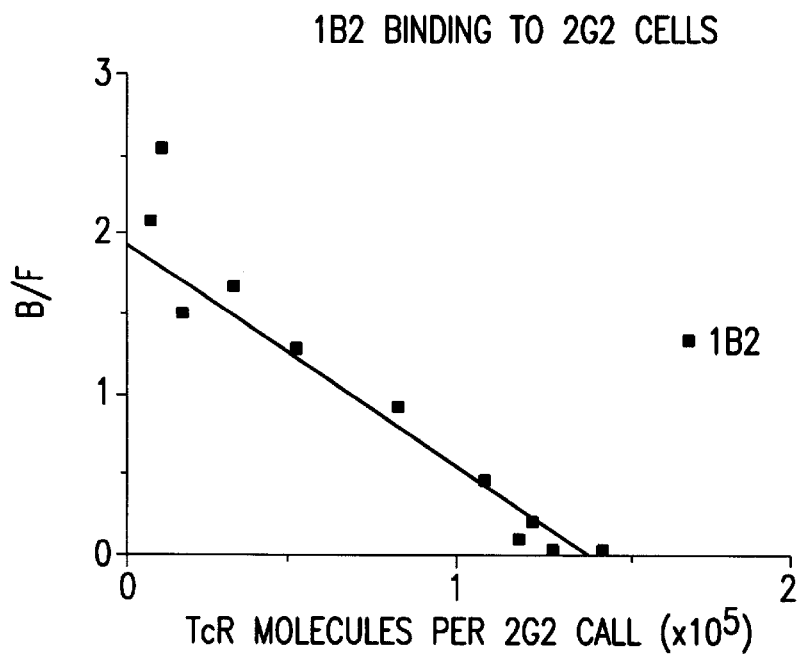
FIGS. 8A–D show a scatchard analysis of GPI-TcR transfectants of 4G4, which were cotransfected with constructs including the pSRα expression vector.
Figure 8B:
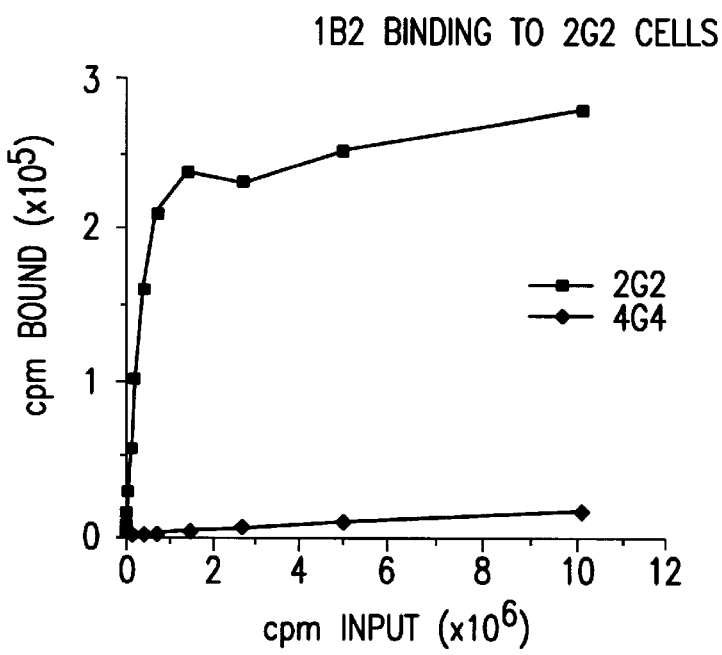
Figure 8C:
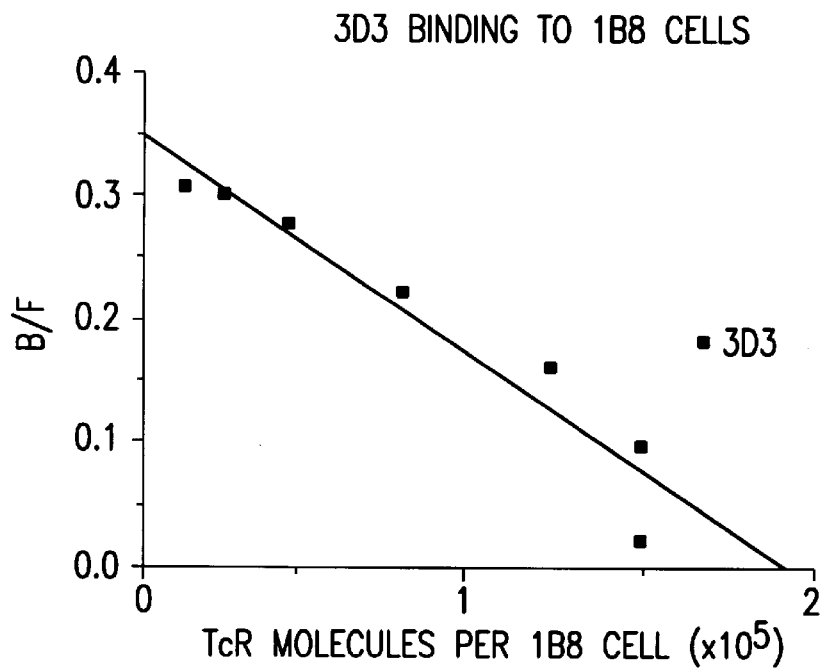
Figure 8D:
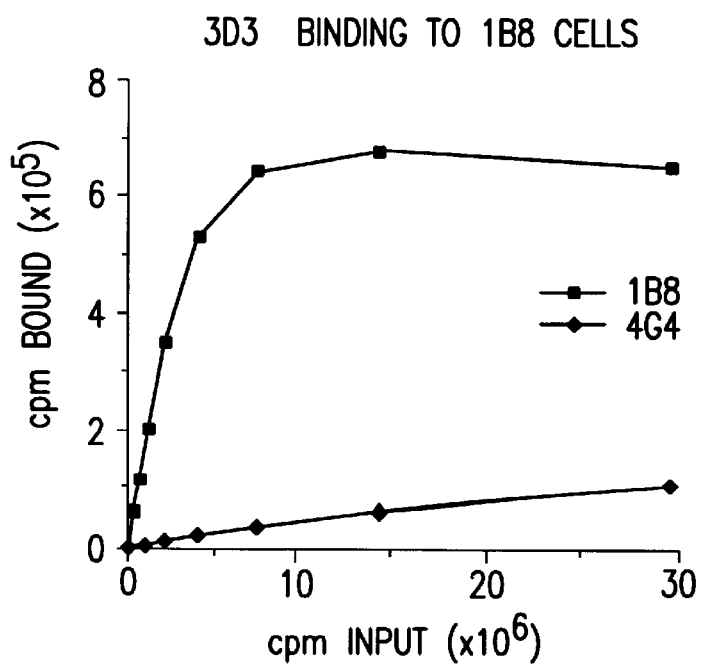

Fifteen out of twenty pFRSV-SRα transfectants of BW5147 selected at 50 nM methotrexate expressed the 1B2 clonotypic epitope while eighteen of these twenty clones expressed the F23.1 Vβ8 epitope. The FACS profile of one of the fifteen clones at 50 nM methotrexate (clone 2C16, as deposited on Jul. 12, 1996 with the American Type Culture Collection, 10801 University Boulevard, Manassas, VA 20110-2209 U.S.A., assigned accession number CRL-12150) is shown in FIGS. 7D–K. The shift in mean fluorescent intensity upon FACS analysis of clone 16 with the 1B2 clonotypic antibody was 1.2 logarithmic units, a shift which is slightly greater (by 0.2 logarithmic units) than the shift observed with 2C (FIGS. 7D–K). The intensity of staining observed in these pFRSV-SRα transfectants is slightly greater than those of the 2C CTL clone and the 2G2 SRα transfectant. One of these transfectants (2C16) was selected for further methotrexate amplification. FACS analysis of this transfectant at 500 µM methotrexate reveals a shift in fluorescent intensity of 3.8 logarithmic units, an intensity of staining which is significantly greater than that of the 2C clone or than any of our previous transfectants (FIGS. 7A–C). Although different FACS machines are used in these experiments, this shift in fluorescent intensity is also two logarithmic units greater than that of the αβHPAP-S expressing CHO cells which have been used by Davis to produce GPI-linked TcR (Lin, et al., 1990). Finally, our 2C16 TcR could be released using PI-PLC (FIGS. 7A–C).

Figure 10A:
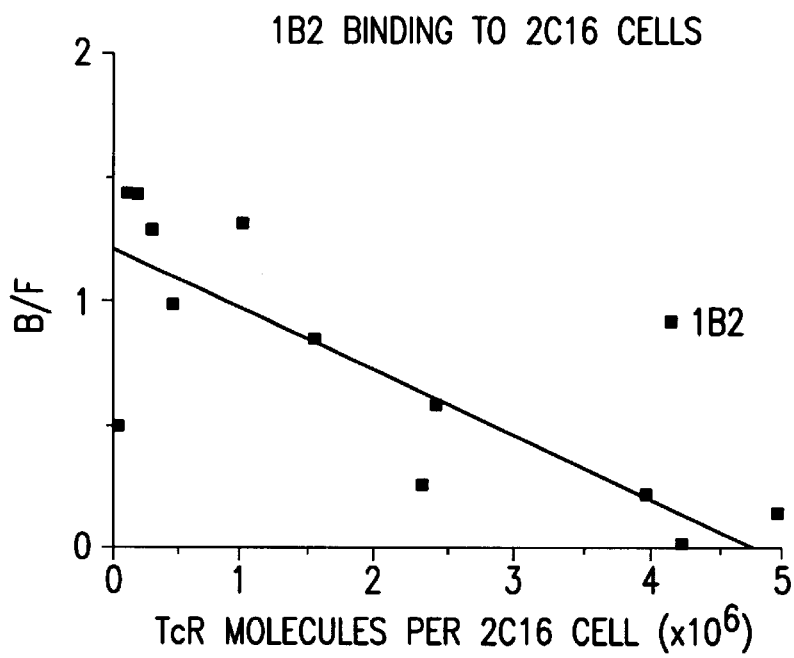
FIGS. 10A–F show a scatchard analysis of GPI-TcR transfectants of BW5147, which were cotransfected with constructs including the pFRSV-SRα expression vector.
Figure 10B:
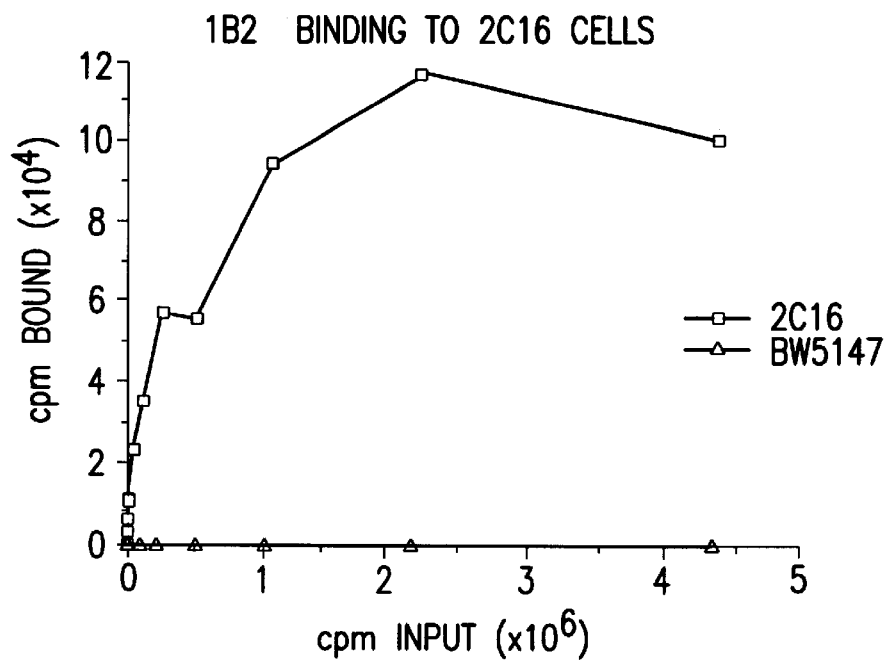
Figure 10C:
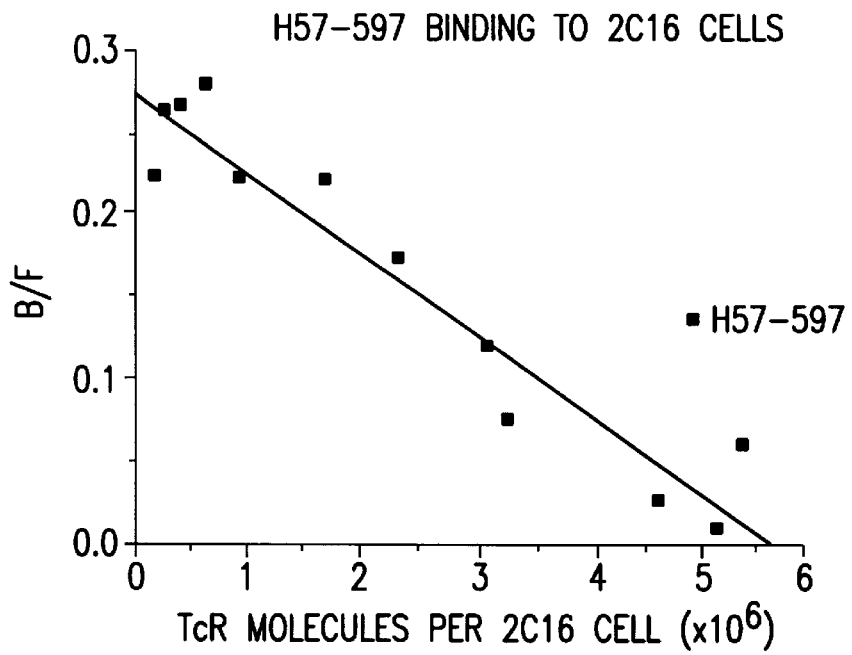
Figure 10D:
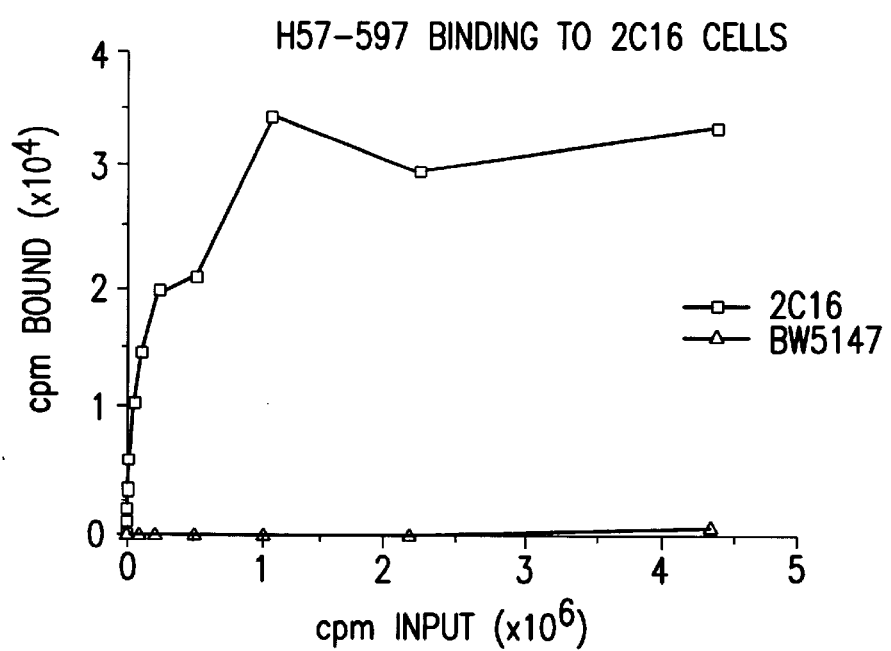
Figure 10E:
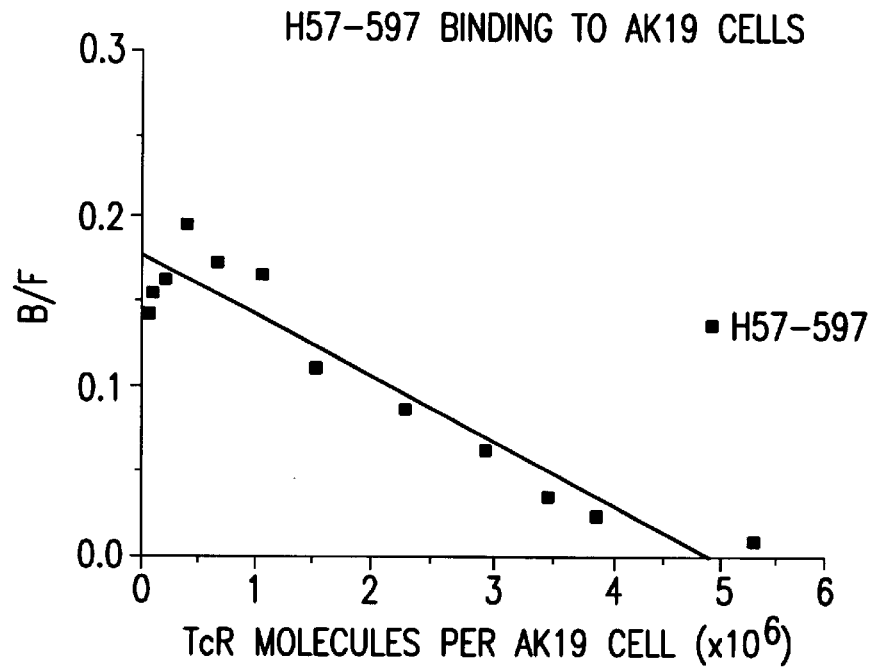
Figure 10F:
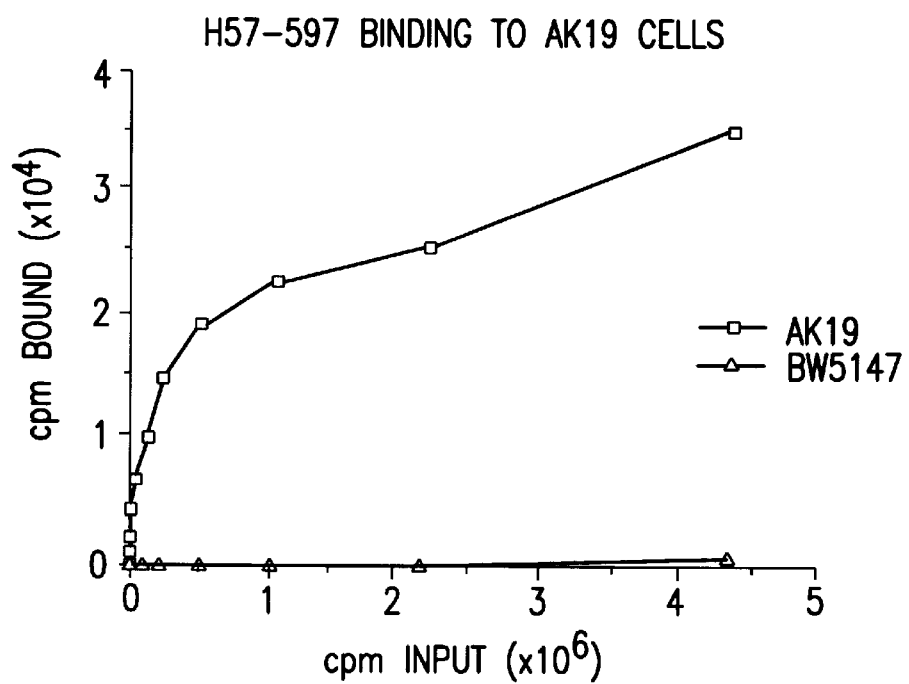

Based upon these encouraging results, αβ/Thy-1 chimeric cDNAs encoding GPI-linked D10 TcR molecules were transferred into the pFRSV-SRα expression vector and a transfectant of BW5147 (AK19) was produced in the same fashion in collaboration with Dr. Ajay Kumar (data not shown). Scatchard analysis on the fully amplified clone 16 with both the 1B2 and H57-597 antibodies indicate that there are $5\times10^6$ GPI-TcR molecules per cell (FIGS. 10A–D). This number GPI-TcR molecules per cell was also observed by Scatchard analysis with the H57-597 antibody on the fully amplified AK19 clone (FIGS. 10E–F). Calculation of the theoretical amount of soluble TcR molecules present in $1\times10^9$ 2C16 or AK19 cells yielded 830 µg. Thus, by placing the strong SRα promoter upstream of the α and β TcR/Thy-1 chimeric genes in conjunction with methotrexate amplification using the mutant DHFR gene in BW5147 cells, protein expression levels on the cell surface were increased 40-fold.

Thus, while we have described what are the presently contemplated preferred embodiments of the present invention, further changes and modifications could be made by those skilled in the art without departing from the scope of the invention, and it is contemplated to claim all such changes and modifications.

We claim:

1. A membrane free heterodimeric, disulfide linked α/β soluble T cell receptor molecule which shares a clonotypic epitope with a native T cell receptor of a parent T-lymphocyte.

2. A solution containing the soluble T-cell receptor as recited in claim 1 in a suitable solvent.

3. The solution as recited in claim 2, wherein said solvent is RPMI medium.

4. The solution of claim 3, wherein said solution contains 0.25 units of said PI-PLC.

5. The membrane free heterodimeric, disulfide-linked α/β soluble T cell receptor of claim 1 having a molecular weight of about 90 kd to about 95 kd in a non-reduced state.

6. A membrane free heterodimeric, disulfide linked α/β soluble T cell receptor molecule which shares a clonotypic epitope with a native T cell receptor of a parent T lymphocyte and which inhibits the alloresponse of the parent T lymphocyte.

7. A membrane free heterodimeric, disulfide linked α/β soluble T cell receptor molecule which binds to an mHc peptide ligand of the parent T lymphocyte.

* * * * *